United States Patent [19]

Furie et al.

[11] Patent Number: 5,252,712

[45] Date of Patent: Oct. 12, 1993

[54] PURIFIED ANTIBODIES WHICH SPECIFICALLY BIND HUMAN ABNORMAL PROTHROMBIN

[75] Inventors: Bruce E. Furie; Barbara C. Furie, both of Wellesley; Rita A. Blanchard, Newton, all of Mass.

[73] Assignee: New England Medical Center Hospitals, Inc., Boston, Mass.

[21] Appl. No.: 227,829

[22] Filed: Aug. 3, 1988

Related U.S. Application Data

[60] Division of Ser. No. 661,187, Oct. 15, 1984, which is a continuation-in-part of Ser. No. 402,318, Jul. 27, 1982, abandoned, which is a continuation-in-part of Ser. No. 198,444, Oct. 20, 1980, abandoned.

[51] Int. Cl.$^5$ .................. C07K 15/28; C12N 5/18
[52] U.S. Cl. .................. 530/389.3; 530/388.25; 435/240.27
[58] Field of Search .................. 530/387, 389.3, 388.25; 436/547; 435/7, 240.27; 935/89, 93, 95, 103, 104

[56] References Cited

PUBLICATIONS

Lewis et al., "Hybridoma-Produced Conformation-Specific Monoclonal Antibodies to Human Prothrombin," Blood (Suppl. 1), 58:220a (Nov. 1981).
Lewis et al., "Conformation-Specific Monoclonal Antibodies Directed Against the Calcium-Stablized Structure of Human Prothrombin," Biochem; 22:948-954 (1983).
Blanchard et al., "Antibodies Specific for Bovine Abnormal (Des-γ-Carboxy) prothrombin," J. Biol. Chem., 254(24):12513-12520 (1979).
Gantdtt et al., "Plasma Prothrombin during Treatment with Dicumarol," Scand. Jour. Clin & Lab. Invest, 22:23-28 (1968).
Blanchard et al., The New England Journal of Medicine, "Acquired Vitamin K-Dependent Carboxylation Deficiency in Liver Disease," 305: 242-248 (1981).
Liebman et al., "Hepatic Vitamin K-Dependent Carboxylation of Blood-Clotting Proteins," Hepatology 2: 488-494 (1982).
Furie et al., "Radioimmunoassays of Species of Human Prothrombin," in Disroders of Thrombin Formation, Colman, ed., 1983, pp. 84-100.
Blanchard et al., "Immunoassays of Human Prothrombin Species which Correlate with Functional Coagulant Activities", J. of Lab. and Clinical Medicine, 101: 242-255 (1983).

(List continued on next page.)

Primary Examiner—David L. Lacey
Assistant Examiner—Susan L. Futrovsky
Attorney, Agent, or Firm—Fish & Richardson

[57] ABSTRACT

Antibodies which form immune complexes with human native prothrombin only, in the presence of mixtures of human native prothrombin and human abnormal prothrombin as well as antibodies which form antibody antigen complexes with human abnormal prothrombin in the presence of such mixtures have been obtained. Immunoassay techniques are used for qualitative and quantitative determinations of these antigens in human plasma or serum. Unique methods of obtaining the antibodies are described including obtaining antibodies to native prothrombin by dissociation of antigen antibody complexes formed in the presence of calcium ions with a material having a greater affinity constant for binding with calcium ions than does prothrombin. Dissociation of the complex in this manner yields human native prothrombin antibodies which are specific and non-reactive with human abnormal prothrombin. A process is described in which assays are applied to the sensitive detection of vitamin K deficiency and various forms of liver disease including hepatocellular carcinoma, and to monitoring of anticoagulant therapy with sodium warfarin. The invention described herein was made in the course of working under a grant from the Department of Health and Human Services.

3 Claims, 5 Drawing Sheets

SPECIFICITY OF ANTIBODIES TO ABNORMAL PROTHROMBIN

OTHER PUBLICATIONS

Blanchard et al., "Subclinical Vitamin K Deficiency in Newborns and their Mothers," Blood, 62: 272a (1983), Abstr. No. 994.

Furie et al., "Clinical Applications for Immunoassays of Abnormal and Native Prothrombin," Hematology, Ann. Mtg. Prog., Dec. 3-6, 1983, pp. 57-59.

Liebman et al., "Des-γ-Carboxy (Abnormal) Prothrombin as a Serum Marker of Primary Hepatocellular Carcinoma," The New England J. of Med., 310: 1427-1431 (1984).

Furie et al., "Comparison of the Native Prothrombin Antigen and the Prothrombin Time for Monitoring Oral Anticoagulant Therapy," Blood, 64: 445-451 (1984).

Krasinski et al., "The prevalence of vitamin K deficiency in chronic gastrointestinal disorders," The American J. of Clin. Nutrition, 41: 639-643 (1985).

Owens et al., "Monoclonal Antibodies against Human Abnormal (Des-γ-carboxy) prothrombin Specific for the Calcium-free Conformer of Prothrombin," The J. of Bio. Chem., 259: 13800-13805 (1984).

Blanchard et al., "Plasma Prothrombin and Abnormal Prothrombin in Antigen," Blood, 58: 231A (1981), Abstr. No. 833.

Blanchard et al., "Acquired Disorders of Hepatic Vitamin K-Dependent Carboxylation of Prothrombin," Clinical Rearch, 29: 516A (1981).

Furie et al., "Antibodies Directed against a γ-Carboxyglutamic Acid-rich Region of Bovine Prothrombin," The J. of Biol Chem., 253: 8980-8987 (1978).

Tai et al., "Conformation-Specific Antibodies as Probes of the Metal Dependent Tertiary Structure of Bovine Prothrombin," Federation Proceedings, 38: Abstr. No. 2970, (1979).

Yelten, et al., "Plasmacytomas and Hybridomas: Development and Applications," in *Monoclonal Antibodies*, ed. by Kennett et al. (Plenum Press), p. 19.

Bynum et al., "Low-Dose Heparin Therapy in the Long-Term Management of Venous Thromboembolism," The American J. of Med. 67: 553-556 (1979).

Ganrot, P. O., et al., Scand. Journ. Clin. & Lab. Invest., 21: 238-244, (1968).

Köhler, G., et al., "Continuous cultures of fused cells secreting antibody of predefined specificity," Nature 256: 495-497, (1975).

Furie, B., et al., "Conformation of the γ-Carboxyglutamic Acid-Rich Region of Prothrombin," Thrombosis & Haem. 42: Abstr. No. 0219 (1979).

Tai et al., "Conformation-specific Antibodies Directed Against the Bovine Prothrombin Calcium Complex," The J. of Bio. Chem. 255: 2790-2795 (1980).

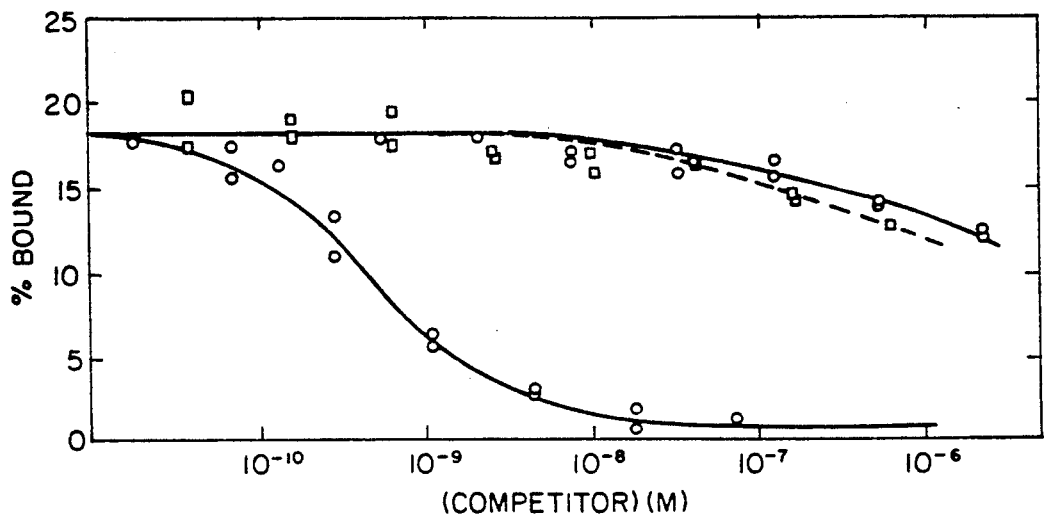
FIG. 1 SPECIFICITY OF ANTIBODIES TO ABNORMAL PROTHROMBIN
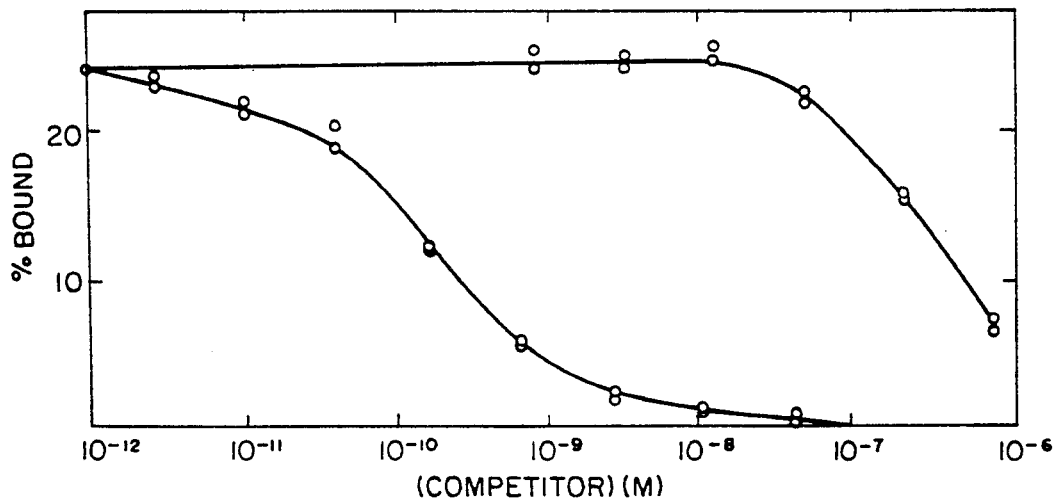
FIG. 2 SPECIFICITY OF ANTIBODIES TO PROTHROMBIN-Ca(II)

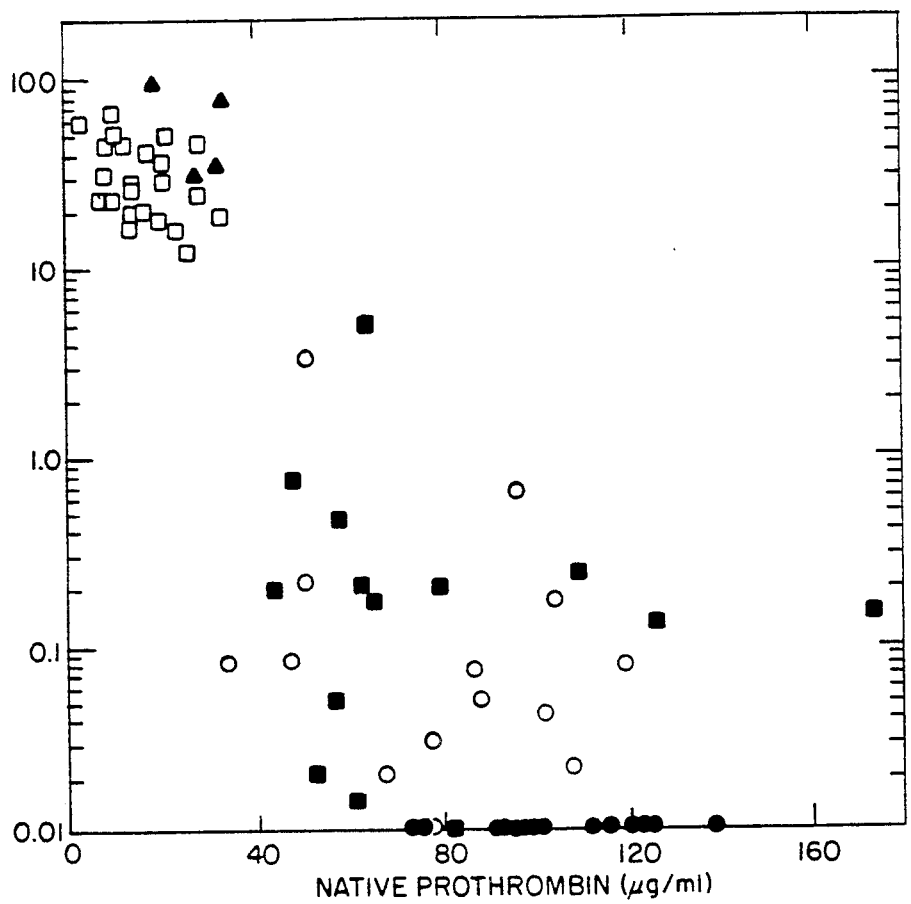
FIG. 3
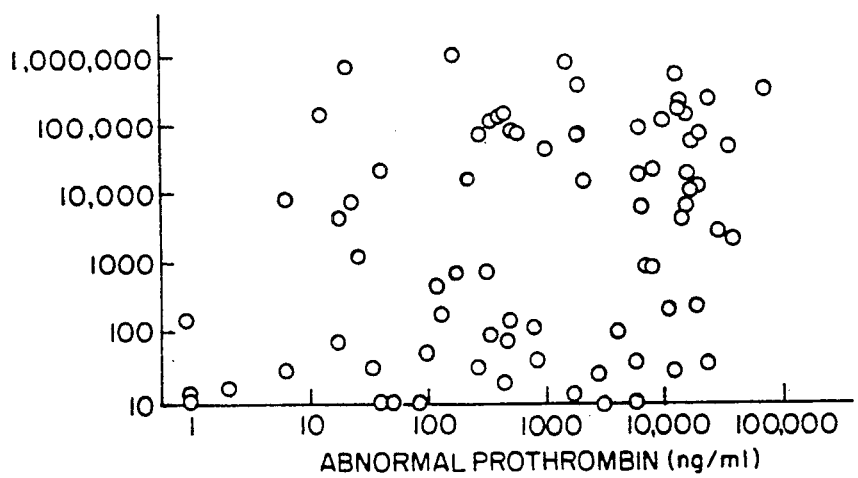
FIG. 8  SERUM CONCENTRATIONS OF ABNORMAL PROTHROMBIN AND
α-FETOPROTEIN IN THE 76 STUDY PATIENTS
VALUES FOR BOTH ANTIGENS ARE PLOTTED ON A LOGARITHMIC
SCALE. THE CORRELATION BETWEEN VALUES FOR ANTIGENS
WAS POOR

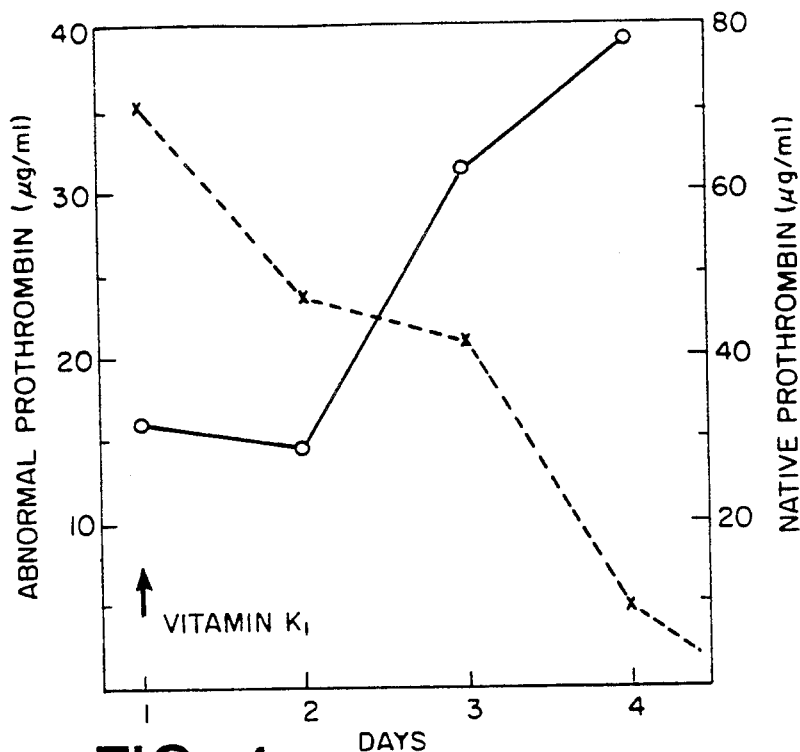
FIG. 4
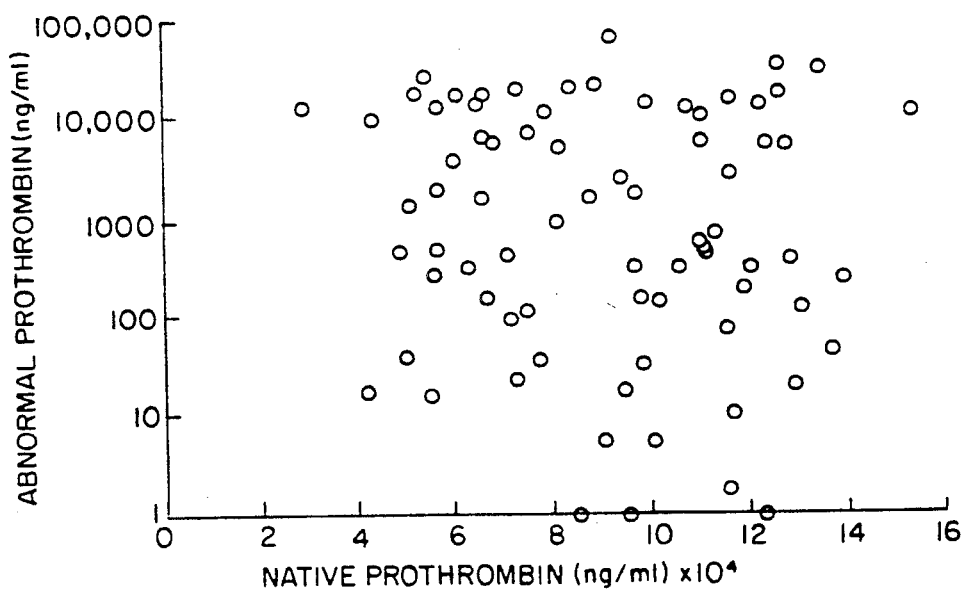
FIG. 5 SERUM CONCENTRATIONS OF ABNORMAL PROTHROMBIN AND NATIVE PROTHROMBIN IN 76 PATIENTS WITH PRIMARY HEPATOCELLULAR CARCINOMA

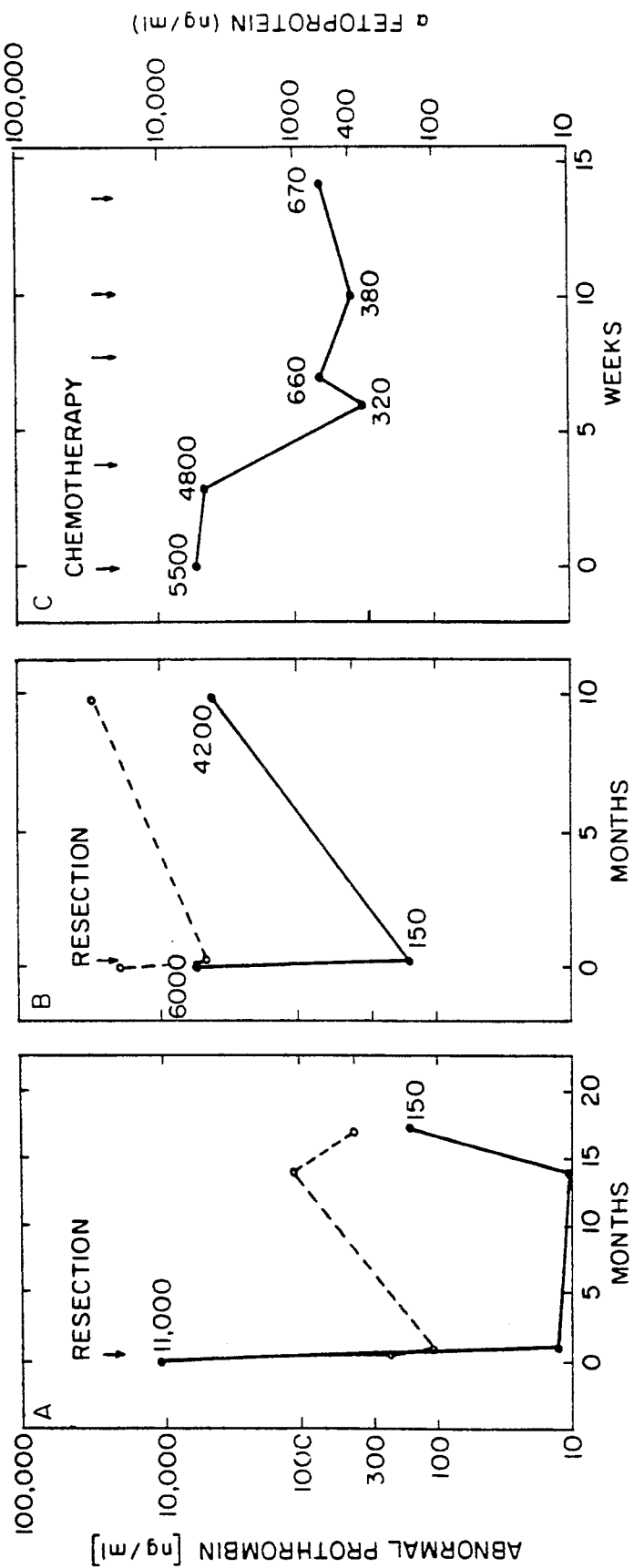
FIG. 6 ABNORMAL-PROTHROMBIN LEVELS (SOLID CIRCLES) AND α-FETOPROTEIN LEVELS (OPEN CIRCLES) DURING TREATMENT OF HEPATOMA. TWO PATIENTS (PANELS A AND B) WERE TREATED WITH SURGICAL RESECTION OF THE TUMOR. ANOTHER PATIENT (PANEL C) RECEIVING COMBINATION CHEMOTHERAPY, HAD α-FETOPROTEIN-ANTIGEN LEVELS CONSISTENTLY LOWER THAN 10 ng PER MILLILITER

PURIFIED ANTIBODIES WHICH SPECIFICALLY BIND HUMAN ABNORMAL PROTHROMBIN

This invention was made with Government support under 5-RO1-HL21543-03 awarded by the National Heart, Lung, and Blood Institute. The Government has certain rights in the invention.

BACKGROUND OF THE INVENTION

This application is a divisional of application Ser. No. 661,187 filed Oct. 15,1984, now issued U.S. Pat. No. 4,769,320, which is a continuation-in-part of application Ser. No. 402,318 filed Jul. 27, 1982 which is a continuation-in-part of application Ser. No. 198,444 filed Oct. 20, 1980, both now abandoned.

Prothrombin is a vitamin K dependent plasma protein involved in the final stages of blood coagulation as has been well-known for some time. It has a molecular weight of about 72,000 and contains about 12% carbohydrate. Prothrombin is a calcium-binding protein that undergoes a conformational transition in the presence of calcium as is known. The proteolytic activation of prothrombin to thrombin is a critical step in normal hemostasis. Prothrombin is synthesized in the liver where a prothrombin precursor undergoes post-translational modification to yield the functional form of prothrombin which is known as "native prothrombin" and contains γ-carboxyglutamic acid. In the presence of vitamin K antagonists, such as sodium warfarin also known as Coumadin, a trademarked product of Endo Laboratories division of DuPont Corp. of Wilmington, Delaware, or in the absence of vitamin K, the prothrombin activity in the blodo may be significantly diminished. This can be measured indirectly by the prothrombin time, a one-stage coagulation assay, or by direct measurement of prothrombin coagulant activity using prothrombin deficient substrate plasma. Severe liver disease may also be associated with low plasma prothrombin activity. Thus impaired synthesis of protein (liver disease), inadequate supplies of vitamin K (vitamin K deficiency) or drugs that inhibit the action of vitamin K (sodium warfarin) lead to diminished plasma prothrombin activity in humans and other mammals.

Coumadin is the trade name for warfarin. When Coumadin is used as an oral anticoagulant as is widely done in the therapy or prevention of thrombotic disease, it lowers the activity of vitamin K dependent blood coagulation proteins such as prothrombin. The appropriate Coumadin dose is established by monitoring the prothrombin time. The prothrombin time is maintained at one and a half to two and a half times that obtained with normal plasma.

In 1968 an altered form of prothrombin known as "abnormal prothrombin" and "human abnormal prothrombin" as opposite to human native prothrombin was discovered in the plasma of human patients treated with sodium warfarin. Abnormal prothrombin has low prothrombin activity but cross reacts with many prothrombin antisera. Abnormal prothrombin from bovine blood was first isolated in 1972. Such abnormal prothrombin was found to have about 3% of the coagulant activity of an equivalent amount of native prothrombin. Otherwise, the molecular weight, carbohydrate composition and amino acid composition of the acid hydrolysate were substantially identical within experimental error. In the early 70's it was discovered that bovine abnormal prothrombin unlike prothrombin does not bind to barium salts and does not bind to calcium ions. It was subsequently shown that the functional differences between abnormal and native prothrombin relate to the structural differences between these proteins and full prothrombin function requires intact calcium binding sites. In the mid-70's it was discovered that a theretofore unknown amino acid γ-carboxyglutamic acid occurred in bovine prothrombin and was lacking in abnormal bovine prothrombin. This amino acid seemed to be required for the full expression of prothrombin coagulant activity. Abnormal prothrombin is known to have no coagulant activity, does not bind metal ions and does not contain γ-carboxyglutamic acid. Other researchers have theorized that prothrombin is synthesized in the liver in a precursor form containing glutamic acid instead of γ-carboxyglutamic acid. A carboxylation process in the liver modifies glutamic acid to form γ-carboxyglutamic acid. This enzyme system requires vitamin K and is inhibited by vitamin K antagonists.

Many efforts have been made in the past to develop quantitative assays for determining the level of prothrombin and abnormal prothrombin in body fluids such as plasma. These methods in the past have had significant limitations. Assays have been difficult to devise in that human abnormal prothrombin and human native prothrombin both have 584 amino acids with 574 of them being identical in the two forms and the 10 remaining differing only by a carboxyl group. Although structurally nearly identical, these proteins have very different functional attributes and play different roles with regard to blood coagulation.

Existing methods of evaluating prothrombin and other proteins in the extrinsic pathway of blood coagulation include conventional prothrombin time determinations. This does not detect abnormal prothrombin levels. Direct assays for prothrombin coagulant activity are carried out by mixing test plasma with varying ratios of prothrombin deficient plasma followed by clotting and comparison with a standard curve. Only functional prothrombin of the native type is thus measured. Cross immunoelectrophoresis measures both abnormal and native prothrombin semi-quantitatively but requires similar concentrations in order to prevent the dominant species from obscuring the other, thus limiting application. Laurell rocket immunoelectrophoresis is another difficult and technically demanding test which does not distinguish between the two types of prothrombin. Radioimmunoassay of prothrombin has been carried out but the antibodies used in the past bind abnormal as well as normal prothrombin equally (or almost equally) and thus only total prothrombin levels are measured which are insufficient for clinical diagnostic purposes. Echis carinatus assays using snake venom are used to measured total prothrombin; in combination with a two-stage prothrombin assay, those assays can be used to estimate the level of abnormal prothrombin indirectly.

None of the above assays offer a direct, quantitative, easily carried out, sensitive and specific assay for either prothrombin in the presence of abnormal prothrombin or abnormal prothrombin in the presence of protrombin particularly in human species. In the present invention, work has been carried out involving conformation specific antibodies to specific regions of the protein surface which has led to the development of immunochemical reagents specific for abnormal prothrombin and for native prothrombin. A process is described in which abnormal prothrombin and native prothrombin are measured in body fluids and permit the diagnosis of particular body disorders.

SUMMARY OF THE INVENTION

It is an object of this invention to provide useful antibodies for forming antibody antigen complexes with human abnormal prothrombin in the present of human native prothrombin and antibodies for forming antigen antibody complexes with human native prothrombin in the presence of human abnormal prothrombin.

Another object of this invention is to provide simplified and useful methods for obtaining antibodies as described in the preceding object which method can be carried out with substantially conventional equipment and without a high degree of complexity.

Still another object of this invention is to provide immunoassay procedures which permit the quantitative determination of human abnormal prothrombin in plasma or serum and human native prothrombin in plasma or serum each in the presence of the other which immunoassay methods are uncomplicated and can be carried out with high degree of precision and sensitivity.

Still another object of this invention is to provide a means and method for detecting the presence or absence of body disorders associated with the presence or absence of human abnormal prothrombin or level of native prothrombin in plasma or serum and the level of such human abnormal prothrombin or native prothrombin enabling the identification and differentiation in certain cases of liver disease, vitamin K deficiency, and/or the regulation of anticoagulant therapy such as the regulation of sodium warfarin applied to the body.

According to the invention a method of determining the presence or absence of body disorder in a mammalian species comprises obtaining a plasma or serum specimen from the mammal to be tested, determining the level of abnormal prothrombin or native prothrombin in the mammalian plasma, with, in humans, the presence of abnormal prothrombin indicating a body disorder. In the preferred form, the determination of abnormal prothrombin and normal prothrombin from a human is made with the use of antibodies specific to each in the presence of the other. When the body disorder is vitamin K deficiency, the level of abnormal prothrombin is monitored and maintained at a predetermined level. Preferably when requesting anticoagulant administration such as administration of warfarin, native prothrombin is monitored as an indication of desired levels of amounts of warfarin to administer. The level of native prothrombin can also be quantitatively determined by this method. During anticoagulation therapy of humans with vitamin K antagonists like warfarin, levels of from 12 micrograms per ml to 24 micrograms per ml of native prothrombin are maintained after quantitative determination of these levels by further administration of the drug in use such as sodium warfarin. Preferably the native prothrombin is maintained at a body fluid level of 10 to 24 micrograms per ml.

According to the invention, a first antibody comprises an antibody specific to human native prothrombin in the presence of calcium and non-reactive with abnormal human prothrombin. A second antibody is specific to form an antibody antigen complex with human abnormal prothrombin in the presence of human native prothrombin and in the presence of absence of calcium. Preferably either of the two antibodies of this invention are reactive to form complexes in body fluids under standard laboratory conditions for in vitro testing such as room temperature, standard atmospheric pressure and normal variations thereof. The antibody specific to human native prothrombin forms complexes therewith in the presence of calcium ions at levels of preferably at least 0.5 millimolar and preferably at a 1 millimolar level of calcium. A method of producing antibodies that bind with human native prothrombin in the presence of calcium and do not bind with human abnormal prothrombin starts out with obtaining antisera to human native prothrombin in a conventional manner. This can be done by injection of human native prothrombin into a conventional host such as rabbit, goat, horse or the like. Reaction is allowed to take place wherein an antiserum is produced and obtained containing human native prothrombin antibody. The antiserum is reacted with human native prothrombin preferably bound to a column matrix to bind the antibody with the human native prothrombin in the presence of calcium ions to form an antibody antigen complex. The complex is washed by eluting the column with a fluid such as EDTA (ethylenediaminetetraacetice acid) having a greater affinity constant for calcium ions that does human native prothrombin thus obtaining an unliganded conformation of prothrombin. Antibodies which only bind to human native prothrombin in the presence of calcium are dissociated from the antigen antibody complex. Preferably the EDTA contains the antibody which can be separated and used for immunoassay procedures. These antibodies bind to native prothrombin but not to abnormal prothrombin.

In the method of producing antibodies that bind with human abnormal prothrombin in the presence of native prothrombin, an antiserum is produced to abnormal prothrombin as previously described in the preceding paragraph. That antiserum is then passed through a column and reacted with human native prothrombin. The material that runs through is then passed over an agarose column which is linked to thermally decarboxylated prothrombin (a synthetic analog of abnormal prothrombin). The material which binds to the column is then eluted from the column with guanidine hydrochloride and the eluted material then dialyzed to remove the guanidine hydrochloride. The material freed of guanidine hydrochloride contains the desired antibody which binds to human abnormal prothrombin in the presence of native prothrombin without binding to the native prothrombin.

In the method of carrying out immunoassys to obtain quantitative and qualitative determinations, conventional immunoassay procedures can be used which include enzyme-linked assays and radioimmunoassays.

The presence or absence of human native prothrombin or human abnormal prothrombin is determined by carrying out an immune reaction on a plasma or serum sample with the appropriate antibody as described above and qualitatively or quantitatively determining the presence or absence of antibody-antigen complexes using conventional procedures.

It is a feature of this invention that it has now been recognized that the presence of human abnormal prothrombin in the body of humans does not occur at level above 0.03 micrograms per ml of plasma, serum or other body fluids except under conditions of liver disease, when individuals are treated with materials such as vitamin K antagonist, in cases of vitamin K deficiencies or as a result of a metabolic defect resulting in impaired carboxylation. In fact levels below 0.03 micrograms per ml of body fluid are believed indicative of such diseases but such lower levels cannot be monitored with the methods of this invention. The presence of any abnormal prothrombin is believed to be indicative of the diseases and disorders noted. Thus, immunoassay techniques can be used to determine the presence or absence of certain liver disease, to distinguish liver disease from certain other malfunctions of the body wherein there is a variation from normal in either both of abnormal prothrombin and native prothrombin, and to determine the amount of sodium warfarin to give patients so as to minimize the risk of thrombosis or bleeding.

In the drawings,

FIG. 1 is a graph showing the specificity of anti-abnormal prothrombin for abnormal prothrombin, compared to native prothrombin.

FIG. 2 is a graph showing the specificity of anti-native prothrombin for native prothrombin, compared to abnormal prothrombin.

FIG. 3 is a graph showing serum concentrations of native and abnormal prothrombin in patients suffering from several medical disorders.

FIG. 4 is a graph showing the effects of vitamin K treatment on native and abnormal prothrombin levels in a patient suffering from vitamin K deficiency.

FIG. 5 is a graph showing serum concentrations of abnormal and native prothrombin in patents with primary hepatocellular carinoma.

FIG. 6 is a series of three graphs showing serum abnormal prothrombin and $\alpha$-fetoprotein concentrations in three hepatoma patients.

FIG. 8 is a graph showing serum abnormal prothrombin and $\alpha$-fetoprotein concentrations in hepatoma patients.

DESCRIPTION OF PREFERRED EMBODIMENTS

Figure 7:
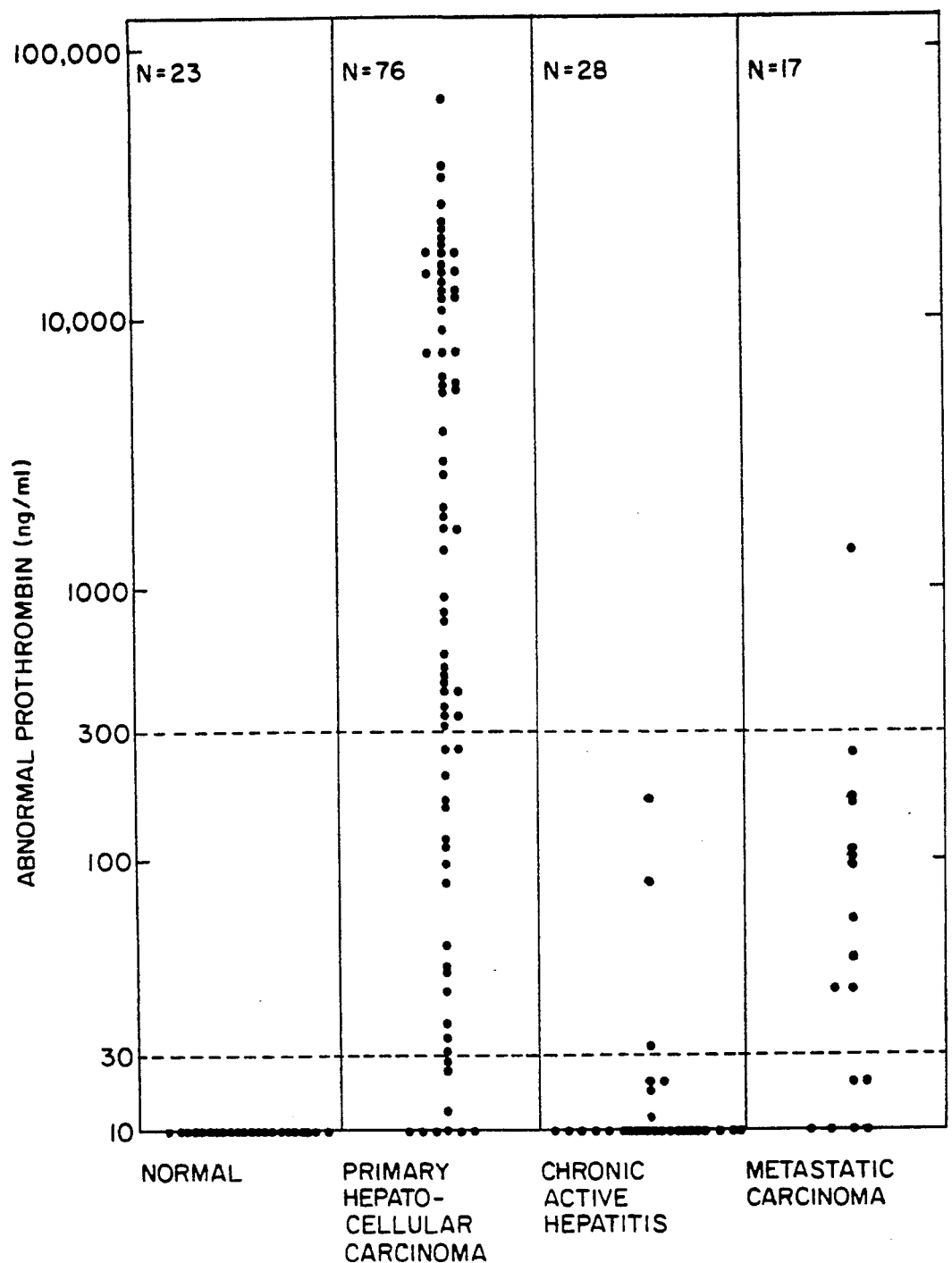
FIG. 7 is a graph showing serum abnormal prothrombin concentrations in patients with three different liver disorders.

The isolation of specific antibodies form immune serum is accomplished by affinity chromatography. This is a general method, attributed to Porath and popularized by Cuatrecasas et al, in which a protein antigen is bound covalently to an inert matrix (e.g. agarose). Antiserum is passed over a column containing protein antigen-agarose; antibody which binds to the antigen-agarose is retained on the column. All other proteins are eluted with washing. Antibodies specific for the protein antigen are eluted from the antigen-agarose column by dissociation of the antigen-antibody complex. Agents often used for these purposes include guanidine HCl, urea, acid (citrate, acetic acid), base (ammonium hydroxide), chaotropic salts (potassium thiocyanate), or free antigen. These methods all involve purification of antibody specific for the antigen. These antibodies can be then applied to an immunoassay to measure the quantity of antigen in a given solution. In the process to be described, a new method of elution of antibody from the affinity matrix is described (ligand elution affinity chromatography) which yields conformation-specific antibody subpopulations specific for the protein conformation that the ligand induces. This method allows for facile purification of antibodies specific for prothrombin and which do not bind to abnormal prothrombin. In a second process, the preparation of antibodies specific for abnormal prothrombin is described. These immunologic reagents are employed in a sensitive, specific assay for each of these prothrombin species in human plasma from patients with various disorders of prothrombin biosynthesis.

A method has been developed to isolate specific antibodies from immune serum that are specific for human abnormal prothrombin (anti-abnormal prothrombin) and human prothrombin (anti-prothrombin-Ca(II). Anti-abnormal prothrombin binds tightly to abnormal prothrombin but interacts minimally while prothrombin. Anti-prothrombin-Ca(II) binds tightly to prothrombin in the presence of calcium but interacts minimal with abnormal prothrombin. These antibody reagents have been incorporated into two separate immunoassays. On measures abnormal prothrombin in plasma despite the presence of prothrombin. The other measures prothrombin in plasma despite the presence of abnormal prothrombin. These assays allow the quantitation of abnormal prothrombin and prothrombin in human plasma. Specific patterns and relationships of levels of abnormal prothrombin and prothrombin correlate to certain disorders of prothrombin biosynthesis. These assays can be used to detect the presence of certain diseases, to monitor therapy with oral anticoagulants, and to distinguish between disorders to prothrombin synthesis and prothrombin catabolism.

In a process for preparation of anti-prothrombin-Ca(II) native human prothrombin in the presence of calcium is preferably injected intradermally into rabbits. The hyperimmune serum obtained, after multiple immunizations, contains antibodies directed against the native conformation of prothrombin. A small proportion of these antibodies bind to prothrombin only in the presence of calcium. Most of the antibodies bind to prothrombin regardless of whether calcium is present or not. Anti-prothrombin antiserum is applied to an affinity column containing prothrombin covalently bound to agarose. This column is previously equilibrated in a buffer system containing calcium chloride. The prothrombin bound to the column assumes the three-dimensional structure (conformation) seen in the prothrombin-calcium complex. It appears that only about 5% of the structure of prothrombin is significantly altered by calcium. The anti-prothrombin antibodies recognize and bind to both the calcium dependent and the calcium independent structures on the prothrombin surface. After all extraneous proteins in the antiserum are washed through, ethylenediaminetetraacetic acid (EDTA) is applied to the column. EDTA remove the calcium from prothrombin, and a small local change in the conformation of prothrombin occurs as the protein reverts to its normal conformation in the absence of metal ions. Conformation-specific antibodies bound to this local region of conformational change can no longer bind to prothrombin, and thus elute from the column. The majority of antibodies remain bound to prothrombin. The eluted antibodies are considered anti-prothrombin-Ca(II) antibodies. They bind to prothrombin in the presence but not in the absence of calcium. They bind to prothrombin in the presence of calcium, but cannot bind to abnormal prothrombin in the presence of calcium because abnormal prothrombin cannot bind calcium and assume the calcium-induced conformation. Other methods exist for preparing an antibody specific for prothrombin. These methods are all based upon recognition that the structure of the antigen (prothrombin or a fragment of prothrombin) is altered by calcium and that the antibody subpopulations are conformation-specific.

In one method, anti-prothrombin antisera is applied to a prothrombin-agarose column equilibrated with EDTA. Antibodies which fail to bind to this column, but will being to a prothrombin-agarose column equilibrated with calcium will also have the same functional characteristics.

In another method, monoclonal antibodies can be prepared by fusion of splenocytes of mice immunized with prothrombin to malignant plasma cell lines in tissue culture (hybridoma). Clones which make a monoclonal antibody that binds to prothrombin in the presence of calcium but not in the absence of calcium will also have the same functional characteristics of anti-prothrombin-Ca(II), i.e., binds to prothrombin but not abnormal prothrombin.

In a process for preparation of anti-abnormal prothrombin antiserum to purified human abnormal prothrombin is raised in rabbits. This antiserum contains antibodies which bind to both abnormal prothrombin and prothrombin. Specific antibodies, which bind to only abnormal prothrombin, are isolated by sequential immunoabsorption using affinity chromatography. The first step entails removal of all anti-abnormal prothrombin antibodies from the antisera by affinity column chromatography using prothrombin covalently bound to agarose. Antibodies which do not bind include those specific for abnormal prothrombin. Using traditional or standard techniques, the next step would involve absorption of the antiserum to an affinity column containing abnormal prothrombin covalently bound to agarose. However, abnormal prothrombin is available in only limited amounts. Therefore, a semi-synthetic equivalent of abnormal prothrombin was prepared. Using the method of Tuhy and Mann, lyophilized human prothrombin is thermally decarboxylated at 110° to yield a heterogeneous material with low quantities of $\gamma$-carboxyglutamic acid and little prothrombin activity. This material, decarboxylated prothrombin, has a significant component analogous to abnormal prothrombin. Decarboxylated prothrombin is coupled to agarose, and employed for the second stage of the affinity purification of anti-abnormal prothrombin. The purified anti-abnormal prothrombin antibodies bind to abnormal prothrombin, but do not bind to prothrombin.

An alternative method for preparation of antibody specific for abnormal prothrombin involves the hybridoma technology. These methods are all based upon recognition that the structure and conformation of local regions of prothrombin and abnormal prothrombin differ. Monoclonal antibodies can be prepared by fusion of splenocytes of mice immunized with abnormal prothrombin to malignant plasma cell lins in tissue culture. Clones which produce a monoclonal antibody that binds to abnormal prothrombin but not to prothrombin can be obtained.

Detection and diagnosis of disorders of prothrombin biosynthesis can be carried out in humans using plasma or serum measurements of abnormal prothrombin and prothrombin.

The specific assays for abnormal and native prothrombin are used in human plasma or serum to determine the status of prothrombin biosynthesis. This information can be correlated to specific disease states.

Normal plasma: Plasma and serum from normal individuals contains no detectable abnormal prothrombin. The sensitivity and specificity of the assay indicate that abnormal prothrombin can be no greater than 0.03 $\mu$g/ml. Native prothrombin at a normal level is about 108 $\mu$g/ml.

Acute Hepatitis: Plasma and serum from patients with acute hepatitis contain quantities of abnormal prothrombin that vary from 0.1 g/ml to 6 $\mu$g/ml or higher. The native prothrombin level is usually normal, but can be above or below the normal prothrombin range.

Cirrhosis: Plasma and serum from patients with alcoholic cirrhosis have elevated abnormal prothrombin. The prothrombin level is usually subnormal.

Chronic Active Hepatitis: Plasma and serum from patients with chronic active hepatitis contain no detectable abnormal prothrombin.

Vitamin K deficiency: Vitamin K deficiency, on the basis of vitamin K malabsorption in the intestine, disorders of the enterohepatic circulation, nutritional deficiency, or antibiotic interference with enteric bacteria, is associated with an elevated abnormal prothrombin and correspondingly low prothrombin. These patients respond to vitamin K.

Metastatic Cancer Involving the Liver: Abnormal prothrombin levels are elevated in patients with cancer involving destruction of the liver.

Hepatocellular Carcinoma: Abnormal prothrombin is uniformly present. Levels a vary from low to very high levels. The level of native prothrombin is normal, but variable.

Monitoring anticoagulants: Patients treated preferably with sodium warfarin have native prothrombin levels between 9 and 30 $\mu$g/ml. Although the prothrombin time is usually employed to regulate warfarin dosage, approximately 20–30% of patients taking warfarin have hemorrhagic or thrombotic complication. Better monitoring of therapy with these assays may alleviate these complications.

Examples of diagnosis aids include:

(a) A patient with a prolonged prothrombin time with abnormal liver function studies may have liver disease or vitamin K deficiency. The presence of high levels of abnormal prothrombin and modestly low levels of prothrombin suggests vitamin K deficiency. Low levels of abnormal prothrombin and normal levels of prothrombin indicate liver disease.

(b) A patient is not feeling well. All hemtologic and renal screening tests are normal. An elevated abnormal prothrombin level indicates occult liver disease.

(c) A hemorrhaging patient with jaundice and significant coagulopathy is found to have an elevated abnormal prothrombin, indicating the diagnosis of liver disease and not intravascular coagulation.

(d) A "normal" individual develops severe bleeding. A prothrombin time is prolonged. The very high abnormal prothrombin and low prothrombin suggest overdosage of warfarin i.e. facitious ingestion of warfarin.

(e) A patient with primary melanoma two years earlier develops general constitutional symptoms. The elevated abnormal prothrombin suggests liver infiltration by cancer.

(f) A patient is treated with warfarin to prevent recurrent thromboembolic disease. The native prothrombin is measure to be 36 $\mu$g/ml, despite a prothrombin time in the therapeutic range. The patient is identified at risk to thrombosis. The daily warfarin dose is increased and the native prothrombin monitored on a regular basis.

The following nonlimiting examples illustrate quantitative determination in plasma of human abnormal (des-$\gamma$-carboxy) prothrombin and human native prothrombin in plasma with specific radioimmunoassay.

Preparation of abnormal prothrombin: Human abnormal prothrombin was purified using a method analogous to that described for the preparation of bovine abnormal prothrombin (Blanchard, R. A. Furies, B. C., and Furie, B. Antibodies for bovine abnormal (des-γ-carboxy-) prothrombin. *J. Biol. Chem.* 254: 12513-12520 (1979). Plasma (330 ml) was collected from patients on chronic sodium warfarin therapy. Plasma was made 25 mM in sodium citrate an 1 mM in benzamidine. BaCl$_2$ (1M) was added dropwise to a final concentration of 80 mM. After stirring for 1 hr at 23°, the precipitate which formed was removed by centrifugation. The plasma supernatant, containing prothrombin forms which do not bind to barium salts, was further purified or DEAE-Sephacel column. Protein was applied in 10 mM potassium phosphate, pH 7.5, 1 mM benzamidine, 0.02% sodium azide to a column (2×6 cm) equilibrate in the same buffer. After washing the column with 10 mM potassium phosphate 1 mM benzamidine, 0.02% sodium azide, pH 7.5, the prothrombin forms were eluted with 0.5M potassium phosphate, 1 mM benzamidine, 0.02% azide, pH 7.5. This fraction was dialyzed into 0.1M boric acid, 1M NaCl, 0.1% Tween 20, 1 mM benzamidine, 0.02% sodium azide, pH 8.5(Smith, J. A. Hurrell, J. G. and Leach, S. J. Elimination of non-specific adsorption of serum proteins by Sepharose-bound antigens. *Anal Biochem*: 87:299–305 (1978), and divided into five equal aliquots. Each aliquot was applied to an antiprothrombin-Sepharose column (1.5×5 cm) equilibrated in the same buffer. Abnormal prothrombin was eluted with 4M guanidine Hcl, 1 mM benzamidine, and dialyzed against 40 mM Tris-HCl, 0.15 NaCl, 1 mM benzamidine, pH 8.0.

Abnormal prothrombin was concentrated in dialysis tubing using dry sucrose and then dry Sephadex G-200. The protein was dialyzed against 40 mM Tris-HCl, 0.15M NaCl, 1 mM benzamidine, 0.02% sodium azide, pH 8.0. Abnormal prothrombin (4.0 mg) was applied to a Sephacryl S-200 column (1.0×100 cm) equilibrated in 40 mM Tris-HCl, 0.15M NaCl, 1 mm benzamidine, 0.2% sodium azide, pH 8.0.

Human prothrombin was prepared from fresh frozen plasma by absorption to and elution from barium citrate, DEAE cellulose chromatography, and heparin-Sepharose chromatography. (Rosenberg, J. S., Beeler, D. L. and Rosenberg, R. D. Activation of prothrombin by highly purified human factors V and Xa in the presence of human antithrombin III. *J. Biol. Chem.* 250:1607-1617. (1975).

Preparation of human decarboxylated prothrombin: Human prothrombin was decarboxylated using the method of Mann. (Tuhy, P. M., Bloom, J. W. and Mann, K. G. Decarboxylation of ovine prothrombin fragment 1 and prothrombin. *Biochemistry* 18:5842-(1979). After incubation of the lyophilized material at 110° for 6 hours, the high molecular weight material which formed was removed by gel filtration on Sephacryl S-200. The product contained less than two mol of γ-carboxyglutamic acid per mol of protein.

Preparation of $^{125}$I-labeled abnormal prothrombin and $^{125}$I-labeled prothrombin. Proteins were labeled with Na$^{125}$I (New England Nuclear) employing Chloramine T, as previously described. (Hunter, W. M. and Greenwood F. C. Preparation of iodine-131 labeled growth hormone of high specific activity. *Nature* 194:495-496. (1961) Lactoperoxidase can be used as for labeling with iodine instead of Chloramine T.

Materials, Goat anti-rabbit immunoglobulin (Cappel Laboratories), bovine albumin (Sigma), and rabbit immunoglobulin (Cappel Laboratories) were obtained commercially. Sepharose 4B, Sephacryl S200, and DEAE-Sephacel were obtained from Pharmacia. Chloramine T, guanidine Hcl, Tween 20, and benzamidine-Hcl were supplied by Eastman, Schwarz/Mann, Fisher, and Aldrich, respectively.

Amino Acid Analysis: Amino acid analyses were performed on a Beckman model 119CL amino acid analyzer equipped with a Beckman model 126 data system. γ-Carboxyglutamic acid determinations were performed on protein hydrolyzed in 2 M KOH for 22 hours at 110°. (Hauschka, P. V., Quantitative determination of γ-carboxyglutamic acid in proteins. *Anal. Biochem.* 80-212-223 (1977).

Human plasma: Fresh frozen human plasma was obtained from the Northeast Regional Red Cross. Fresh human plasma was also obtained from donors on chronic sodium warfarin therapy. Blood samples, anticoagulated in citrate (9 parts blood, 1 part 3.8% citrate) were collected from normal subjects and patients medicated with sodium warfarin. Alternatively serum can be obtained by clotting and separating whole blood and used in placed of plasma.

Preparation of Agarose Derivatives for Affinity Chromatography: Sepharose 4B was activated with cyanogen bromide (Eastman; 200 mg/ml Sepharose) using standard methods. (Furie, B., Provost, K., Blanchard, R. A. and Furie, B. C. 1978. Antibodies directed against a γ-carboxyglutamic acid-rich region of bovine prothrombin. *J. Biol. Chem.* 253:8980-8987.) Prothrombin, decarboxylated prothrombin or anti-prothrombin antibodies in Nacl/Pi (0.2M potassium phosphate, 0.13M NaCl), pH 7.4, was coupled to the activated Sepharose using ratios of 3.0 mg of polypeptide to 1.0 ml of activated Sepharose. Columns of derivatized Sepharose were stored at 4°.

Preparation of Anti-prothrombin-Ca(II) antibodies: Anti-prothrombin-Ca(II) antibodies were prepared by a modification of the method previously described. (Tai, M. M., Furie, B. C., and Furie, B., Conformation-specific antibodies directed against the bovine prothrombin calcium complex. *J. Biol. Chem.* 255:2790-2795 (1980). Rabbit anti-human prothrombin antiserum (4 ml) was applied to a human prothrombin-Sepharose column (2×7 cm) equilibrated with 40 mM Tris-Hcl, 0.15M NaCl, 1 mM CaCl$_2$, pH 8.1. A small amount of antibody was eluted with 40 mM Tris-HCl, 0.15M NaCl, 3 mM EDTA, pH 8.1, and considered anti-prothrombin-Ca(II) antibodies. the antibody was concentrated by ultrafiltration using a PM 30 membrane. The remaining antibodies were eluted with 4M guanidine HCl.

Preparation of Anti-abnormal prothrombin antibodies: Antibodies to human abnormal prothrombin were raised in rabbits using standard methods. (Blanchard, R. A., Furie, B. C., and Furie, B. Antibodies specific for bovine abnormal (des-γ-carboxy-) prothrombin. *J. Biol. Chem.* 254;12513-012520 (1979). Anti-abnormal prothrombin antiserum (4 ml) was passed over a prothrombin-Sepharose column (2×7) equilibrated in 40 mM Tris-Hcl, 0.15M NaCl, pH 8.1. Antiserum which failed to bind was applied to a decarboxylated prothrombin-Sepharose column (1.5×7.0 cm) equilibrated in 0.1M boric acid, 1 M NaCl, 0.1% Tween 20, pH 8.5. Bound antibody, anti-abnormal prothrombin-specific, was eluted with 4M guanidine HCl, pooled, dialyzed against 40 mM Tris-HCl, 0.1M NaCl, pH 8.1, and concentrated by ultrafiltration using a PM 30 membrane.

Preparation of anti-human prothrombin 1 antibodies; Antibodies which bound both prothrombin and abnormal prothrombin equivalently were isolated from rabbit anti-human prothrombin antiserum. As a by-product of isolation of anti-prothrombin-Ca(II) antibodies, the prothrombin antibody fraction which bound to prothrombin in the presence of EDTA and eluted with guanidine HCl was employed. After dialysis, this antibody preparation was applied to a bovine prethrombin 1-Sepharose column (1.2×10 cm) equilibrated in 0.1M boric acid, 1M NaCl, 0.1% Tween 20, pH 8.5. The peak which bound was eluted with 4M guanidine HCl and dialyzed. This antibody preparation is directed against antigenic determinants shared by bovine and human prothrombin 1. The preparation of the bovine prothrombin 1-Sepharose has been previously described. (Furie, B. Provost, K., Blanchard, R. A. and Furie, B. C. Antibodies directed against a γ-carboxyglutamic acid-rich region of bovine prothrombin. *J. Biol. Chem* 253:8980-8987 (1978). Radioimmunoassay - Direct binding assay: The interaction of purified antibody with $^{125}$I-labeled prothrombin or $^{125}$I-labeled abnormal prothrombin was studied using an immunoassay. The bound and free antigen were separated by the double antibody technique. The reaction mixture included $^{125}$I-labeled protein ($1\times10^{-10}$M), antibody ($10^{-12}$ to $10^7$M), albumin (20 mg/ml), 40 mM Tris-HCl, 0.15 M NaCl, pH 8.1, and 1 mM benzamidine in a volume of 255 μl. With anti-prothrombin-Ca (II) antibodies, solutions were adjusted to 1 mM Ca(II). With anti-abnormal prothrombin and anti-prethrombin 1 antibodies, solutions were adjusted to 1 mM EDTA. After incubation for 16 hours at 4°, 25 μl of goat antirabbit immunoglobulin (Cappel; 12 mg/ml) was added. Rabbit immunoglobulin, 20 μl (Cappel; 2 mg/ml) was added 30 minutes later. The solution was incubated for 4 hours at 25° and assayed in toto for $^{125}$I. The precipitate which formed was removed by centrifugation in a Beckman model 4 B Microfuge, washed twice with 40 mM Tris-HCl, 0.15M NaCl, pH 8.1, 1 mM benzamidine, and assayed for $^{125}$I. $^{125}$I assays were performed in a Beckman Gamma 8000 gamma scintillation spectrometer.

Radioimmunoassay - Competition Assay: The displacement of $^{125}$I-labeled prothrombin or abnormal prothrombin from anti-prothrombin-Ca(II) antibodies, anti-abnormal prothrombin antibodies, or anti-prethrombin 1 antibodies by prothrombin or abnormal prothrombin was studied using a competition radioimmunoassay. As above, the double antibody technique was employed. The reaction mixtures included $^{125}$I-labeled prothrombin ($1\times10^{-10}$M) or abnormal prothrombin ($1\times10^{-10}$M); anti-prothrombin-Ca(II) ($3.2\times10^{-10}$M), anti-abnormal prothrombin ($7.2\times10^{-9}$M), or anti-prothrombin 1 ($2\times10^{-9}$M); albumin (20 mg/ml); 40 mM Tris-HCl, 0.15 M NaCl, pH 8.1, 1 mM benzamidine; unlabeled prothrombin or abnormal prothrombin was studied using a competition radioimmunoassay. As above, the double antibody technique was employed. The reaction mixtures included $^{125}$I-labeled prothrombin ($1\times10^{-10}$M) or abnormal prothrombin ($1\times10^{-10}$M); anti-prothrombin-Ca(II) ($3.2\times10^{-10}$M), anti-abnormal prothrombin ($7.2\times10^{-9}$M), or anti-prethrombin 1($2\times10^{-9}$M); albumin (20 mg/ml); 40 mM Tris-Hcl, 0.15 M NaCl, pH 8.1, 1 mM benzamidine; unlabeled prothrombin or abnormal prothrombin or citrated plasma diluted into 1 mg/ml albumin, as indicated. Solutions were adjusted to 1 mM CaCl$_2$ for anti-prothrombin-Ca(II) antibodies and to 1 mM EDTA for anti-abnormal prothrombin and anti-prethrombin 1 antibodies. The total volume was 255 μl. Solutions were incubated and the percentage of $^{125}$I bound to antibody determined as indicated in the direct binding assay.

RESULTS

Preparation of human abnormal prothrombin: Abnormal prothrombin was purified from plasma obtained from patients treated chronically with sodium warfarin. The purification scheme, analogous to that previously employed to isolate bovine abnormal prothrombin (Blanchard, R. A., Furie, B. C., and Furie, B. Antibodies specific for bovine abnormal (des-γ-carboxy-) prothrombin *J. Biol. Chem.* 254:12513-12520 (1979) is based upon affinity chromatography using anti-prothrombin antibodies. These antibodies bind to both prothrombin and abnormal prothrombin. After DEAE-Sephacel chromatography of the barium citrate supernatant, the abnormal prothrombin preparation was further purified by anti-prothrombin-agarose affinity chromatography and Sephacryl S-200 gel filtration. The purified material yielded a single band when subject to disc gel electrophoresis or gel electrophoreses in dodecyl sulfate. Abnormal prothrombin was radiolabeled with $^{125}$I using chloramine T. The gel profile of $^{125}$I-labeled abnormal prothrombin after gel electrophoresis in dodecyl sulfate contains only 1 peak. Abnormal prothrombin appeared greater than 95% pure by these criteria. Clotting activity of human abnormal prothrombin as measured by the prothrombin assay was less than 1% of that expected from a similar quantity of purified human prothrombin, but had a comparable activity to prothrombin when assayed by the E. carinatus assay.

Purification of antibodies specific for abnormal prothrombin: Anti-serum to purified abnormal prothrombin was raised in rabbits. These anti-abnormal prothrombin antibodies formed precipitating complexes with both abnormal prothrombin and prothrombin. The anti-abnormal prothrombin antiserum was applied to a prothrombin-agarose column to remove antibodies which bound prothrombin. A first peak was obtained, depleted of antibodies which bind to prothrombin and was applied to a decarboxylated prothrombin-agarose column. Antibodies which bound to the decarboxylated prothrombin-agarose column, anti-abnormal prothrombin-specific antibodies, could be eluted with 4M guanidine HCl. These antibodies were dialyzed and concentrated. These antibodies represented less than 5% of the original anti-abnormal prothrombin antibodies.

Purification of antibodies specific for prothrombin: Antibodies specific for the prothrombin-Ca(II) complex were purified by methods similar to those used to prepared antibodies specific for the bovine prothrombin-Ca(II) complex (Tai, M. M., Furie, B. C., and Furie, B. Conformation-specific antibodies directed against the bovine prothrombin calcium complex. *J. Biol. Chem.* 255:2790-2795 (1980). In brief, rabbit anti-human-prothrombin antiserum were applied to a prothrombin-agarose column equilibrated in 1 mM CaCl$_2$. The antibodies which eluted with 3 mM EDTA were considered anti-prothrombin-CA(II) antibodies.

Specificity of anti-abnormal prothrombin antibodies: The interaction of purified anti-abnormal prothrombin antibodies with prothrombin and abnormal prothrombin was evaluated using a radioimmunoassay. In the direct binding assay, anti-abnormal prothrombin antibodies were incubated with $^{125}$I-labeled abnormal prothrombin or $^{125}$I-labeled prothrombin. The free antigen was separated from antibody-bound antigen using the double antibody technique. The binding of the antibody to antigen was observed only with abnormal prothrombin. No significant binding of antibody to prothrombin was observed under the conditions employed.

Using a competition radioimmunoassay, the displacement of $^{125}$I-labeled abnormal prothrombin from anti-abnormal prothrombin antibodies by abnormal prothrombin or prothrombin was evaluated. These antibodies do not bind to prothrombin. In contrast abnormal prothrombin effected complete displacement of $^{125}$I-labeled abnormal prothrombin from the antibody. These experiments indicate that, although abnormal prothrombin and prothrombin are structurally similar, the anti-abnormal prothrombin antibodies have nearly absolute specificity for abnormal prothrombin. The limit of sensitivity of the assay is about $3 \times 10^{-11}$M (2 ng/ml) for abnormal prothrombin.

Measurement of Abnormal Prothrombin: The assay for abnormal prothrombin was optimized to determine the degree of cross-reactivity of anti-abnormal prothrombin antibodies with prothrombin. Because the measurement of abnormal prothrombin in plasma or serum would usually be performed in the presence of significant concentrations of prothrombin, it was anticipated that the limits of the assay would not depend upon assay sensitivity but upon cross-reactivity of antibody with prothrombin.

The interaction of anti-abnormal prothrombin antibodies with abnormal prothrombin and prothrom bin in the competition assay using $^{125}$I-labeled abnormal prothrombin was determined, using concentrations of prothrombin exceeding those in plasma. At concentrations greater than 14 $\mu$g/ml, prothrombin displaced labeled abnormal prothrombin from antibody. Although this degree of cross-reactivity is small (0.01%), it does indicate that the measurement of trace levels of abnormal prothrombin in plasma containing normal levels of prothrombin (100 $\mu$g/ml) must consider this cross-reactivity. For example, when the prothrombin concentration is 150 $\mu$g/ml, the abnormal prothrombin concentration must be in significant excess 15 ng/ml or the abnormal prothrombin concentration must be corrected for the prothrombin contribution to the measurement.

The ability of normal plasma and plasma obtained from a patient on chronic warfarin therapy to displace $^{125}$I-labeled abnormal prothrombin from anti-abnormal prothrombin was also explored. A normal plasma sample, with a prothrombin concentration of 133 $\mu$g/ml (vide infra), contained little, if any abnormal prothrombin. The small displacement observed in undiluted or minimally diluted normal plasma samples can be completely accounted for on the basis of antibody cross-reactivity with prothrombin. In contrast, plasma in patients treated with warfarin effect significant displacement of $^{125}$I-labeled abnormal prothrombin from anti-abnormal prothrombin. These results indicate that this immunoassay permits quantitation of abnormal prothrombin in the presence of prothrombin. Plasma from patients treated with warfarin have significant concentrations of abnormal prothrombin. Normal plasma contains no detectable abnormal prothrombin. Given the present assay system, one can estimate an upper limit of abnormal prothrombin in normal plasma as 30 ng/ml.

Specificity of anti-prothrombin-Ca(II): The specificity of anti-prothrombin-Ca(II) antibodies for prothrombin can be shown using a direct binding assay and a completion radioimmunoassay. In the direct binding assay, the interaction of anti-prothrombin-Ca(II) antibodies with prothrombin and abnormal prothrombin can be evaluated. These antibodies bound to prothrombin in the presence of calcium, but did not bind to prothrombin in the presence of EDTA. It is believed that these antibodies, like those against bovine prothrombin (Tai, M. M., Furie, B. C., and Furie, B. Conformation-specific antibodies directed against the bovine prothrombin calcium complex. *J. Biol. Chem.* 255;2790-2795 (1980)) are conformation-specific for a conformer of prothrombin stabilized by metal ions. These antibodies bound to prothrombin but did not bind to abnormal prothrombin.

The displacement of $^{125}$I-labeled prothrombin from anti-prothrombin-Ca(II) antibody by prothrombin or abnormal prothrombin was investigated. Under the conditions employed, prothrombin coupled completely displace $^{125}$I-labeled prothrombin from antibody. However, no displacement was observed with abnormal prothrombin except at concentrations in excess of about $3 \times 1^{-8}$M. From these data it would appear that the degree of reactivity of anti-prothrombin-Ca(II) antibodies with abnormal prothrombin is about 0.04% that of prothrombin.

Measurement of prothrombin: The concentration of prothrombin in normal plasma and plasma obtained from a patient treated with warfarin was determined by a radioimmunoassay employing anti-prothrombin-Ca(II) antibodies. Using a competition assay, normal plasma and warfarinized plasma were used to displace $^{125}$I-labeled prothrombin from anti-prothrombin-Ca(II) antibodies. Normal plasma can completely displace labeled antigen from antibody. Based upon a standard curve prepared using solutions containing known concentrations of prothrombin, a prothrombin concentration of 133 $\mu$g/ml was estimated in this sample. Similar studies were performed with plasma obtained from a patient treated with warfarin. The plasma concentration of prothrombin was 8.2 $\mu$g.

Concentration of abnormal prothrombin and prothrombin in normal plasma and plasma obtained from patients treated with warfarin: The abnormal prothrombin and prothrombin concentration of plasma from fifteen normal subjects was measured using the two radioimmunoassays described. Standard curves for both assays were established using dilutions of antigen in bovine serum albumin, 20 mg/ml. All determinations were performed in triplicate, these determinations the cross-reactivity of the antibody populations was considered. Concentrations are presented in terms of $\mu$g per ml of citrated plasma. Corrections have not been made for the 10% dilution of plasma introduced by the citrate anticoagulant.

As shown in Table I, attached, fifteen normal individuals have no detectable abnormal prothrombin in their plasma (<0.03 $\mu$g/ml). The level of prothrombin in plasma of these subjects varied from 72 $\mu$g/ml to 140 $\mu$g/ml. The average value was 103±19 $\mu$g/ml. Individual plasma prothrombin determinations, after sample dilution, were reproducible to less than 10%, primary source of error was the 4000-fold plasma dilution required for the radioimmunoassay of prothrombin in normal plasma. It is estimated that the experimental error in the assay is 20% using ou current technique.

TABLE I

Concentration of Abnormal Prothrombin and Prothrombin Normal Plasma

|    | Prothrombin (μg/ml) | Abnormal Prothrombin (μg/ml) | Total Prothrombin Species (μg/ml) |
|----|---------------------|------------------------------|-----------------------------------|
| 1  | 139 ± 4             | 0.0*                         | 140 ± 26                          |
| 2  | 112 ± 6             | 0.0                          | 105 ± 0                           |
| 3  | 125 ± 6             | 0.0                          | 127 ± 16                          |
| 4  | 116 ± 1             | 0.0                          | 127 ± 12                          |
| 5  | 121 ± 9             | 0.0                          | 112 ± 8                           |
| 6  | 73 ± 11             | 0.0                          | 107 ± 6                           |
| 7  | 96 ± 11             | 0.0                          | 137 ± 6                           |
| 8  | 91 ± 7              | 0.0                          | 108 ± 3                           |
| 9  | 77 ± 10             | 0.0                          | 115 ± 18                          |
| 10 | 121 ± 5             | 0.0                          | 135 ± 10                          |
| 11 | 97 ± 4              | 0.0                          | 117 ± 16                          |
| 12 | 91 ± 8              | 0.0                          | 92 ± 5                            |
| 13 | 81 ± 3              | 0.0                          | 110 ± 5                           |
| 14 | 98 ± 9              | 0.0                          | 105 ± 14                          |
| 15 | 102 ± 2             | 0.0                          | 135 ± 18                          |
| Average | 102.5 ± 19.3   |                              | 117.4 ± 13.7                      |

*Not detected. Lower limits of detectable abnormal prothrombin in this assay system was 0.03 μg/ml.

A competition radioimmunoassay employing anti-prethrombin 1 antibodies was used to measure the total of all prothrombin species. This antibody bind similarly to abnormal prothrombin and prothrombin (data not shown). As shown in Table I, the total concentration of prothrombin species in all 15 plasmas corresponds reasonably well to the concentration of prothrombin in these samples. For the most part, the differences between these measurements can be explained by the variation introduced by dilution error.

The plasma abnormal prothrombin and prothrombin concentrations of 10 patients treated with warfarin were determined (Table II). The plasma samples studied has prothrombin times between 1 ½ and 2½ times that of the normal control. The abnormal prothrombin concentrations varied these samples between 17 and 67 μg/ml. The average concentration was 35±14 μg/ml. The protrombin concentration varied between 9 and 30 μg/ml. The average concentration of prothrombin was 16±8μg/ml. The total prothrombin concentration, measured using anti-prethrombin 1 antibodies, varied between 52 and 86 μg/ml. This is a significant finding since it demonstrates that the warfarin causes an absolute decrease in the total concentration of the prothrombin species. Furthermore, the disparity between the sums of the abnormal prothrombin and protrombin concentrations of normal plasma and plasma from patients taking warfarin is not due to a large fraction of a protrombin species which is not measured in either of the specific assays. However, given the degree of reproducibility of the data, we cannot eliminate the possibility that a small fraction of prothrombin species are not detected.

TABLE II

Concentration of Abnormal Prothrombin and Prothrombin in Plasma Obtained From Patients Treated With Warfarin

|    | Prothrombin (μg/ml) | Abnormal Prothrombin (μg/ml) | Total Prothrombin Species (μg/ml) |
|----|---------------------|------------------------------|-----------------------------------|
| 1  | 12 ± 1              | 27 ± 2                       | 64 ± 13                           |
| 2  | 30 ± 1              | 37 ± 0                       | 57 ± 6                            |
| 3  | 9 ± 1               | 17 ± 2                       | 59 ± 2                            |
| 4  | 17 ± 1              | 28 ± 1                       | 55 ± 3                            |
| 4  | 11 ± 1              | 30 ± 4                       | 62 ± 5                            |
| 6  | 30 ± 3              | 33 ± 1                       | 52 ± 2                            |
| 7  | 9 ± 1               | 67 ± 9                       | 86 ± 10                           |
| 8  | 18 ± 1              | 45 ± 3                       | 69 ± 7                            |
| 9  | 13 ± 1              | 42 ± 1                       | 73 ± 8                            |
| 10 | 14 ± 1              | 25 ± 1                       | 60 ± 4                            |
| Average | 16.3 ± 7.9     | 35.0 ± 14.0                  | 63.7 ± 10.0                       |

The final stages of prothrombin biosynthesis involve the carboxylation of selected glutamic acid residues on a prothrombin precursor (Stenflo, J. and Suttie, J. W., vitamin K-dependent formation of γ-carboxyglutamic acid. Ann. Rev. Biochem. 46:157–172 (1977)). These reactions, which take place in the liver, are catalyzed by a carboxylase that requires reduced vitamin K, oxygen and carbon dioxide. Within this hepatic microsomal system, γ-carboxyglutamic acid is synthesized. In the presence of vitamin K antagonists such as warfarin or in the absence of vitamin K, plasma contains species of prothrombin (abnormal prothrombins) deficient in γ-carboxyglutamic acid. These forms may be quantitated by crossed immunoelectrophoresis when the concentration of abnormal prothrombins and prothrombin are similar. (Ganrot, P. O. and Nilehn, J. E., Plasma prothrombin during treatment with dicoumarol. Demonstration of an abnormal prothrombin fraction, Scand. J. Clin. Invest. 22, 23–28 (1968)). When one form predominates, the minor form cannot be accurately assessed. For this reason two separate radioimmunoassays have been developed, one specific for abnormal prothrombin and the other specific for native prothrombin, to study prothrombin biosynthesis during anticoagulant therapy and the abnormalities of vitamin K-dependent carboxylation in certain hepatic nutritional, and hemostatic disorders.

Abnormal prothrombin and prothrombin are identical proteins except that in prothrombin ten glutamic acids residues in the amino terminal domain are carboxlyated to γ-carboxyglutamic acid. Sequencing the NH$_2$-terminus of bovine abnormal prothrombin shows it to be identical to bovine prothrombin except for the presence of glutamic acid instead of γ-carboxyglutamic acid. As might be expected, antibodies prepared against abnormal prothrombin bind to both prothrombin and abnormal prothrombin. Conversely, antibodies prepared against prothrombin bind equivalently to both abnormal prothrombin and prothrombin. To obtain immunologic reagents with absolute specificity for each of these proteins, antibody subpopulations have been isolated from these antisera using sequential immunoabsorption and affinity chromatography.

For anti-abnormal prothrombin-specific antibodies, prothrombin and decarboxylated prothrombin are used as immunoabsorbants. There were three advantages for the use of decarboxylated prothrombin instead of abnormal prothrombin: (1) it is prepared from high purity prothrombin and thus contains no other proteins as contaminants; (2) whereas abnormal prothrombins are heterogeneous with regard to γ-carboxyglutamic acid contents decarboxylated prothrombin could be prepared which contained less than 2 mol of γ-carboxyglutamic acid per mol of protein, (3) unlike abnormal prothrombin decarboxylated prothrombin is available in quantity. It should be emphasized that the decarboxylated prothrombin is in itself structurally heterogeneous and in part distorted. Although anti-abnormal prothrombin-specific antibodies are prepared using decarboxylated prothrombin as an immunoabsorbant, these antibodies bind abnormal prothrombin with a higher binding constant, $K_A$, than they do decarboxylated prothrombin. Since the thermal decarboxylation may cause some alteration of the antigenic structure of the decarboxylated prothrombin, this material was not used as immunogen in preparation of anti-des-$\gamma$-carboxy prothrombin antibodies.

The purification of antibodies specific for prothrombin was based on a different affinity chromatographic approach. A metal-stabilized conformation of prothrombin is assumed by prothrombin covalently bound to agarose when the matrix is equilibrated with buffers containing calcium. When calcium ions are removed, the prothrombin tertiary structure is altered. Antibodies specific for the prothrombin-Ca(II) complex can then be eluted. These antibodies bind prothrombin, but not abnormal prothrombin, in the presence of metal ions. The metal ions can be calcium or others such as manganese and metals in the lanthanium series of the periodic charts. In this radioimmunoassay for prothrombin, the interesting properties of this anti-prothrombin subpopulation have been exploited.

In these studies it has been established that the normal level of human native prothrombin in plasma is $102 \pm 19$ $\mu$g/ml, although others have found different results.

It would appear that under normal physiological conditions the hepatic carboxylation proceeds efficiently since no abnormal prothrombin is detectable in normal plasma. In the plasma of patients treated with warfarin, abnormal prothrombin becomes a majority component of the prothrombin species. Although the abnormal prothrombin level varies depending upon the amount of warfarin administered, the prothrombin level is usually maintained between 9 and 30 $\mu$g/ml in patients with prothrombin times in the therapeutic range. The total prothrombin concentration was $64 \pm 10$ $\mu$g/ml.

The following examples describe specific immunoassays for human plasma abnormal des-$\gamma$-carboxy) prothrombin and human native (carboxylated) prothrombin. These antigens are examined in a variety of disease states in which prothrombin biosynthesis is potentially disturbed. Disorders of carboxylation and disorders of hepatic prothrombin synthesis can be distinguished. Patients with cirrhosis, hepatitis, and vitamin K deficiency, as well as patients treated with vitamin K antagonists, have impaired vitamin K-dependent carboxylation of prothrombin.

A subpopulation of the anti-prothrombin antibodies—anti-prothrombin-Ca(II)—binds to prothrombin only in the presence of Ca(II). They are specific for a conformer of prothrombin that is stabilized by metal ions (Tai, M. M., Furie, B. C., Furie, B., Conformation-specific antibodies directed against the bovine prothrombin calcium complex, J. Biol. Chem. 1980; 255:2790-5). Since abnormal prothrombin does not bind calcium, these antibodies can recognize native prothrombin but not abnormal prothrombin. The specificity of anti-prothrombin-Ca(II) antibodies for prothrombin was shown in a competition radioimmunoassay FIG. II. Radiolabeled prothrombin was displaced from anti-prothrombin-Ca(II) by abnormal prothrombin (solid circles) and by prothrombin (open circles). (See also FIG. I, which illustrates the same sort of specificity of anti-abnormal prothrombin.) Prothrombin could completely displace $^{125}$I-labeled prothrombin from antibody. No displacement was observed in competition with abnormal prothrombin except at concentrations of abnormal prothrombin in excess of $3 \times 10^{-8}$M. From these data, the degree of reactivity of anti-prothrombin-Ca(II) antibodies with abnormal prothrombin is about 0.04 percent that of prothrombin. These experiments indicate that anti-prothrombin-Ca(II) antibodies can be used to measure native prothrombin despite the presence of abnormal prothrombin.

The concentrations of abnormal prothrombin and native prothrombin in plasma from 15 normal subjects were measured with the two radioimmunoassays described above. Standard curves for both assays were established with dilutions of antigen in bovine serum albumin. All determinations were performed in triplicate. None of the normal controls had detectable abnormal prothrombin in their plasma ($<0.03$ $\mu$g per milliliter). The level of native prothrombin in plamsa of these subjects varied from 72 to 140 $\mu$g per milliliter (average value, $108 \pm 19$ $\mu$g per milliliter).

The plasma concentrations of abnormal prothrombin and native prothrombin in 23 patients treated with warfarin were determined (Table II). The plasma samples studied had prothrombin times between 1½ and 2½ times those of the control samples. The concentrations of abnormal prothrombin in these samples ranged from 12 to 65 $\mu$g per milliliter. The prothrombin concentration ranged from 3 to 33 $\mu$g per milliliter. The total prothrombin concentration, measured with anti-prethrombin 1 antibodies (an antibody that binds equivalently to prothrombin and abnormal prothrombin species) ranged from 39 to 87 $\mu$g per milliliter. This is an important finding since it demonstrates that warfarin causes an absolute decrease in the total concentration of the prothrombin species. The sums of the concentrations of abnormal prothrombin and native prothrombin in plasma samples from patients trated with warfarin are about 20 percent less than the total prothrombin concentration in these samples. This finding indicates that most of the prothrombin species can be measured in either of the specific assays. Since the abnormal prothrombin species in plasma are heterogeneous, and since the antibody was raised against an abnormal prothrombin with restricted heterogeneity, it is likely that this antibody does not bind equivalently to all abnormal prothrombins. Therefore, the level of abnormal prothrombin must be considered a lower limit.

TABLE III

Clinical Characteristics and Laboratory Values of Patients Given Sodium Warfarin.

| PATIENT NO. | Age Sex | PRIMARY DIAGNOSIS | WARFARIN DOS mg/day | OTHER MEDICATIONS | PROTHROMBIN TIME sec | ABNORMAL PROTHROMBIN µg/ml | NATIVE PROTHROMBIN µg/ml | TOTAL PROTHROMBIN µg/ml |
|---|---|---|---|---|---|---|---|---|
| 1 | 45/F | Cerebrovascular accident | 8.3 | None | 20.9 | 25 | 14 | 60 |
| 2 | 47/M | Thrombophiebitis | 5 | None | 21.2 | 43 | 13 | 80 |
| 3 | 46/F | Mitral stenosis | 3.2 | Digoxin, iron sulfate | 21.0 | 16 | 14 | 49 |
| 4 | 56/F | Aortic-valve replacement | 6.25 | Quinidine, digoxin, methyldopa, chlorthalidone, tolbutamide | 18.0 | 18 | 20 | 62 |
| 5 | 34/M | Aortic-valve replacement | 6.25 | Digoxin, furosemide, aminophylline | 17.0 | 16 | 23 | 78 |
| 6 | 23/F | Thrombophlebitis, pulmonary embolism | 10.0 | None | 29.0 | 56 | 3 | 70 |
| 7 | 26/M | Thrombophlebitis, pulmonary embolism | 10.7 | None | 23.5 | 23 | 9 | 47 |
| 8 | 49/F | Prior coronary-artery bypass, cerebral embolism | 4.2 | None | 24.0 | 47 | 12 | 73 |
| 9 | 50/F | Mitral stenosis, mitral-valve replacement | 10.0 | Digoxin, potassium chloride, furosemide | 19.0 | 290 | 19 | 63 |
| 10 | 67/M | Aortic-valve replacement | 5.7 | Hydrochlorothiazide, digoxin, allopurinol | 21.0 | 23 | 11 | 55 |
| 11 | 44/F | Mitral stenosis | 3.5 | Digoxin, quinidine, penicillin, theophylline-quarfenesin, hydrochlorothiazide, nitroglycerin | 22.5 | 30 | 9 | 53 |
| 12 | 63/M | Thrombophlebitis, pulmonary embolism | 6.25 | Digoxin, potassium chloride, hydralazine, furosemide | 19.5 | 19 | 33 | 74 |
| 13 | 31/M | Evan's syndrome, thrombophlebitis, pulmonary embolism | 3.3 | Hydrochlorothiazide, propranolol, prednisone | 22.5 | 29 | 21 | 87 |
| 14 | 30/M | Subclavian thrombosis | 7.5 | None | 20.1 | 12 | 26 | 80 |
| 15 | 33/F | Lupus erythematosus, venous thrombosis | 2.0 | Digoxin, predisone, ethacrynic acid | 29.2 | 40 | 17 | 58 |
| 16 | 71/F | Mitral-valve replacement | 5.0 | Digoxin, furosemide, theophylline | 26.5 | 65 | 10 | 59 |
| 17 | 38/M | Wegener's granulomatosis, pulmonary embolism | 12.5 | Cyclophosphamide, prednisone | 19.2 | 50 | 22 | 69 |
| 18 | 65/M | Thrombophlebitis, pulmonary embolism, idiopathic pulmonary fibrosis | 5.0 | Digoxin, quinidine, prednisone | 24.3 | 28 | 14 | 39 |
| 19 | 68/F | Arterial embolism | 2.25 | Propranolol, digoxin, spironolaclone hydrochlorothiazide | 18.5 | 19 | 17 | 49 |
| 20 | 58/F | Cerebral emobolus | 3.75 | Hydrochlorothiazide | 20.0 | 43 | 28 | 82 |
| 21 | 34/M | Cerebrovascular accident | 12.5 | None | 22.0 | 26 | 29 | 49 |
| 22 | 80/F | Rheumatic heart disease, atrial fibrillation | 5.0 | Digoxin, furosemide | 22.0 | 22 | 13 | 59 |
| 23 | 69/F | Mitral-valve replacement, atrial fibrillation | 2.5 | Digoxin, hydrochlorothiazide | 17.0 | 37 | 19 | 65 |

*Average daily dose.

Abnormal prothrombin and native prothrombin were measured in plasma obtained from patients with disorders known to be frequently associated with impaired clotting activity. These data are presented graphically on a semilogarithmic plot of the plasma abnormal prothrombin against the plasma native prothrombin for each subject (FIG. III) showing plasma concentrations of abnormal prothrombin and native prothrombin. Abnormal prothrombin is presented on the ordinate with a logarithmic scale, and native prothrombin on the abscissa with a linear scale. Patients treated with sodium warfarin are represented by open squares (Table III), patients with hepatitis by open circles (Table IV), patients with cirrhosis by solid squares (Table IV), patients with vitamin K deficiency by triangles, and normal controls by solid circles. The abnormal prothrombin varied over four order of magnitude, from the normal level (<0.03 µg per milliliter) to 100 µg per milliliter in a patient with vitamin K deficiency. The warfarin-treated patients are clustered within a narrow native-prothrombin range. Their abnormal-prothrombin levels exceeded the native-prothrombin levels. The four patients with severe vitamin K deficiency are clustered in the same general region. In one of these four patients, who was treated with vitamin K, serial samples were obtained daily for four days. The effects of therapy on native prothrombin and abnormal prothrombin in this patient are presented in FIG. VI where abnormal prothrombin is represented by the dashed line, and native prothrombin by the solid line. These data indicated a half-life of 2.7 days for abnormal prothrombin in plasma, which is comparable to that of prothrombin (Shapiro, S. S., Marinez, J., Human prothrombin metabolism in normal man and in hypocoagulable subjects, J. Clin. Invest. 1969; 48:1292-8).

TABLE IV

Clinical Characteristics and Laboratory Values of Patients with Liver Disease.

| PATIENT NO | Age/Sex | DIAGNOSIS | BILIRUBIN mg/dl | SGOT U/liter | SGPT U/liter | ALKALINE PHOSPHATASE U/liter | SERUM ALBUMIN g/dl | PROTHROMBIN TIME sec | ABNORMAL PROTHROMBIN µg/ml | NATIVE PROTHROMBIN µg/ml |
|---|---|---|---|---|---|---|---|---|---|---|
| 1 | 44/F | Hepatitis | 15.1 | 1400 | 810 | 255 | 2.8 | 14.8 | 0.08 | 34 |
| 2 | 22/M | Hepatitis | 5.1 | 980 | 1720 | 106 | 4.1 | 11.7 | 0.03 | 78 |
| 3 | 36/M | Hepatitis | 8.9 | 212 | 384 | 448 | 2.3 | 15.3 | 0.08 | 48 |
| 4 | 29/F | Hepatitis | 2.3 | 312 | 2440 | 198 | 2.5 | 12.7 | 0.04 | 102 |
| 5 | 56/F | Hepatitis | 5.8 | 1490 | 1230 | 291 | 3.0 | 13.0 | 3.3 | 52 |
| 6 | 38/M | Hepatitis | 2.0 | 189 | 383 | 79 | 3.9 | 12.0 | 0.62 | |
| 7 | 45/M | Hepatitis | 1.9 | 46 | 96 | 86 | 3.9 | 11.8 | 0.07 | 120 |
| 8 | 26/F | Hepatitis | 1.7 | 770 | 1130 | 233 | 4.2 | 12.3 | 0.00 | 78 |
| 9 | 35/M | Hepatitis | 2.4 | 137 | 343 | 74 | 4.3 | 12.3 | 0.02 | 114 |
| 10 | 29/M | Hepatitis | 4.0 | 170 | 455 | 131 | 4.1 | 11.2 | 0.07 | 87 |
| 11 | 26/M | Hepatitis | 4.8 | — | 1770 | 301 | 4.8 | 10.7 | 0.05 | 89 |
| 12 | 27/M | Hepatitis | 1.8 | 108 | 14 | 191 | 2.8 | 15.1 | 0.21 | 46 |
| 13 | 46/M | Hepatitis | 2.1 | 144 | 172 | 265 | 3.6 | 11.9 | 0.17 | 105 |
| 14 | 26/M | Hepatitis | 1.0 | 1275 | 461 | 92 | 4.4 | 12.7 | 0.02 | 68 |
| 15 | 36/M | Cirrhosis | 7.8 | 52 | 18 | 130 | 1.6 | 16.9 | 5.0 | 64 |
| 16 | 63/M | Cirrhosis | | 55 | 21 | 181 | 2.5 | 13.5 | 0.2 | 80 |
| 17 | 52/F | Cirrhosis | 0.9 | 23 | 15 | 125 | 3.9 | 13.0 | 0.14 | 173 |
| 18 | 39/M | Cirrhosis | 8.2 | 44 | 11 | — | 2.6 | 18.0 | 0.05 | 57 |
| 19 | 51/F | Cirhosis | 38.0 | 71 | 28 | 62 | 2.8 | 20.9 | 0.2 | 44 |
| 20 | 59/M | Cirrhosis | 15.4 | 119 | 86 | 90 | 2.4 | 18.9 | 0.7 | 48 |
| 21 | 49/F | Cirrhosis | 4.2 | 42 | 12 | 61 | 2.7 | 14.5 | 0.2 | 63 |
| 22 | 68/M | Hemochromatosis, cirrhosis | 4.9 | 53 | 22 | 154 | 1.5 | 21.2 | 0.23 | 110 |
| 23 | 51/M | Cirrhosis | 1.5 | 17 | 10 | 59 | 4.5 | 13.9 | 0.13 | 127 |
| 24 | 58/M | Cirrhosis | 5.1 | 56 | 33 | 83 | 2.6 | 14.6 | 0.00 | 82 |
| 26 | 65/M | Cirrhosis | 1.2 | 42 | 23 | 121 | 2.3 | 19.0 | 0.44 | 58 |
| 27 | 65/M | Cirrhosis | 2.2 | 52 | 12 | 222 | 2.8 | 13.5 | 0.02 | 54 |
| 28 | 35/M | Cirrhosis | 3.4 | | | 110 | 2.7 | 16.4 | 0.17 | 66 |
| Normal values | | | <1.0 | <40 | <30 | <90 | 3.5–5.0 | 11.0–12.5 | 0.00 | 108 |

Serum aspartate aminotransferase.
Patient was receiving vitamin K therapy.
Serum alanine aminotransferase.
To convert to micromoles per liter multiply by 17 10
Diagnosis was confirmed histologically.

Hemostatic disorders are common complicating features of liver disease. Even in the absence of a bleeding disorder, prolongation of the prothrombin time and the partial thromboplastin time may be manifestations of inadequate synthesis of clotting proteins. The prolonged prothrombin time often associated with liver disease was investigated and found to be due to impaired synthesis of a nascent polypeptide chain, so that the total and native-prothrombin levels are diminished, or due to impaired hepatic post-translational modification of the precursor form of prothrombin, with diminished carboxylation manifested as increased plasma abnormal prothrombin.

The plasma samples of 14 patients with acute hepatitis were examined FIG. III & Table IV. Four patients (29 percent) had prolonged prothrombin times. These patients had elevated abnormal-prothrombin levels (range, 0.08 to 3.3 µg per milliliter). The other 10 patients (71 percent) had normal prothrombin times, and nine of these 10 had elevated abnormal prothrombin (range, 0.01 to 0.62 µg per milliliter). There appeared to be no clear correlation between the level of plasma abnormal prothrombin and those of the serum aspartate and alanine aminotransferases (serum glutamic oxaloacetic and pyruvic transaminases). Overall, 13 of 14 patients (93 percent), whose disorders ranged from the subclinical to the moderately severe, had elevated abnormal prothrombin.

The plasma of 14 with cirrhosis (Table VI) also contained abnormal prothrombin FIG. III. All these patients had prolonged prothrombin times. The plasma levels of abnormal prothrombin ranged from 0 to 5.0 µg pr milliliter. Seven of these patients received vitamin K therapy, which neither corrected the prothrombin time nor decreased the level of abnormal prothrombin. Only one of the 14 patients had undetectable abnormal prothrombin, and 13 (93 percent) had measurable levels.

Table V is a chart illustrating in micrograms per ml of body serum the level of abnormal prothrombin determined by the competitive immunoassays of this invention in humans having the diseases noted. The number of individuals tested is indicated at N in each group.

TABLE V

| | ABNORMAL PROTHROMBIN, MICROGRAMS PER ML | | | | | |
|---|---|---|---|---|---|---|
| | 0.01 | 0.1 | 1 | 10 | 100 | 1000 |
| NORMAL | □ | | | | | N = 15 |
| HEPATOCELLULAR CARCINOMA | □ □□□□ □ | □ □□□□□□ □ | □ □□□□□□□□□□ □ | □□□□□□□□□□ □□□□□□□□□□ □□ | □ | N = 69 |
| BILIARY CIRRHOSIS | □ □ □□□□□□□□ | □□ □ | □□□ □ | □ | | N = 54 |
| CHRONIC ACTIVE HEPATITIS | □ □□□ | □ □ | | | | N = 27 |
| ACUTE HEPATITIS | □ | □□□□ □□ | □ | □ | | N = 14 |
| CIRRHOSIS | □□ | □□ □□□□□ | □ □ | □ | | N = 14 |
| VITAMIN K DEFICIENCY | | □ | □ □□□ | □□ □□□□□ | □□ | N = 17 |

During treatment with warfarin, abnormal (des-γ-carboxy) prothrombin circulates in the blood. Specific radioimmunoassay can be used to assay the plasma abnormal prothrombin, native prothrombin and total prothrombin to evaluate 700 separate samples from 160 patients treated chronically with warfarin. Plasma levels of these prothrombin species were correlated with complications of therapy. A summary of these data is presented in Table VI.

TABLE VI

|  | Patient PT Control PT | APT (μg/ml) | NPT (μg/ml) |
| --- | --- | --- | --- |
| Warfarin-treated | 1.5-3.0 | 35 ± 16 | 17 ± 8 |
| No complications |  |  |  |
| Hemorrhagic complications |  |  |  |
| 1.33 F, ankle hemarthrosis | 2.5 | 56 | 3.0 |
| 2.72 M, elbow and jaw hematoma | 2.3 | 98 | 2.5 |
| 3.43 F, cerebellar hemorrhage | 5.5 | 144 | 6.0 |
| 4.79 F, hematuria, GI bleeding | 3.2 | 42 | 3.4 |
| 5.54 M, hematuria, hematemesis, purpura | 3.5 | 71 | 2.0 |
| 6.30 M, hematuria | 2.7 | 28 | 7.7 |
| 7.52 F, GI bleeding | 2.2 | 44 | 1.5 |
| 8.59 M, epistaxis | 2.3 | 77 | 6.7 |
| Thrombotic complications |  |  |  |
| 1.60 F, arterial occlusion | 2.4 | 104 | 24 |
| 2.42 M, CVA | 1.5 | 32 | 33 |
| 3.37 M, pulmonary embolus | 1.7 | 47 | 45 |
| 4.41 F, pulmonary embolus | 2.4 | 118 | 14 |
| Normal subjects | 1.0 | 0 | 108 ± 19 |

The prothrombin time varied inversely with the level and directly with the abnormal prothrombin level. The degree of anticoagulation, as monitored by the prothrombin time, correlated closely to the native prothrombin. The therapeutic native prothrombin antigen range was determined to be 9 to 30 but preferably 12 to 24 μg/ml. Eight patients had hemorrhagic complications; 5 of 8 had prothrombin times in the therapeutic range but low native prothrombin. Four patients had thrombotic complications; 4 of 4 had prothrombin in therapeutic range but elevated native prothrombin. Of 12 patients with warfarin-related complications, the prothrombin time identified 4/12 (25%) at risk while the native prothrombin antigen identified 11/12 (92%). These results indicate the promise of the native prothrombin antigen assay for monitoring of oral anticoagulation therapy. When native prothrombin levels fall below 12 micrograms per ml the patient is at risk to a bleeding disorder and the warfarin dose is decreased until a stable native prothrombin level is obtained in the 12 to 24 microgram range. Conversely, when the level is above 24 micrograms the warfarin dose is increased.

DISCUSSION

We have established that the normal level of prothrombin in plasma is 108±19 μg per milliliter. This observation is comparable to the results of Lox et al (Lox, C. D., Strohm, G. H., Corrigan, J. J. Jr., Radioimmunoassay of human prothrombin—the quantitation of plasma factor II antigen, Am. J. Hematol. 1978; 4:261-7), who measured prothrombin levels of 86±8 μg per milliliter with a radioimmunoassay using whole anti-prothrombin antiserum, and to those of Ganrot and Nilehn (Ganrot, P. O., Nilehn, J. E., Immunochemical determination of human prothrombin, Scand. J. Clin. Lab. Invest. 1968; 21:238-44), who determined the normal prothrombin concentration to be 60 to 100 μg per milliliter with rocket immunoelectrophoresis. McDuffie et al obtained a value of 154 μg per milliliter (McDuffie, F. C., Giffin, C., Niedringhaus, R., et al., Prothrombin, thrombin and prothrombin fragments in plasma of noraml individuals and of patients with laboratory evidence of disseminated intravascular coagulation, Thromb. Res. 1979; 16:759-73).

Under normal physiologic conditions hepatic carboxylation proceeds efficiently, since no abnormal prothrombin is detectable in normal plasma. The plasma of patients treated with warfarin, abnormal prothrombin becomes the predominant component of the prothrombin species. Although the level of abnormal prothrombin varies with the amount of warfarin administered, the level of native prothrombin is usually maintained between 9 and 30 μg per milliliter in patients with prothrombin times in the therapeutic range. The total prothrombin concentration in these patients treated with warfarin was found here to be 64±13 μg per milliliter although some others have reported different amounts.

There is here direct evidence that patients with different types of liver disease have impaired vitamin K-dependent carboxylation of prothrombin. Regardless of the presence of a clinical bleeding disorder or the status of the prothrombin time, over 90 percent of these patients had detectable under-carboxylated prothrombin in their plasma. Treatment with vitamin K did not alter the level of abnormal prothrombin, thus excluding the possibility of vitamin K deficiency. The mechanisms for diminished vitamin K-dependent carboxylation are unclear. On the one hand, hepatic necrosis may be associated with the premature release of intracellular uncarboxylated prothrombin precursors into the plasma. On the other hand, patients with liver disease may have a vitamin K-dependent carboxylase deficiency. Since some of these patients had only minimal elevations in their serum transaminases, it is probable that the role of acquired carboxylase deficiency is important. Since abnormal-prothrombin antigen is not detectable in normal plamsa but is measurable in most patients with liver disease, this antigen could be useful in screening for hepatic dysfunction. The overlapping clinical presentations of patients with severe liver disease and patients with mild liver disease and vitamin K deficiency may be distinguished by assays of abnormal prothrombin and native prothrombin in plasma. Although both disorders are characterized by a prolongation of the prothrombin time and partial thromboplastin time, patients with vitamin K deficiency have very high levels of abnormal prothrombin, whereas patients with liver disease have lower levels. Although abnormal prothrombin may be a marker of liver disease, the impaired vitamin K-dependent carboxylation that causes its appearance is not so uniformly extensive as to preclude circulation of adequate quantities of native prothrombin. Therefore, prolongation of the prothrombin time is etiologically unrelated to prothrombin biosynthesis in the patients whom we examined. It will remain important to evaluate the biosynthesis of the other vitamin K-dependent proteins with analogous methods to determine the particular hepatic disorder responsible for the hemostatic abnormalities. The above examples starting with the last purification of abnormal prothrombin were described in "Acquired Vitamin K-Dependent Carboxylation Deficiency in Liver Disease", Rita A. Blanchard, M.D., Barbara C. Furie, Ph.D., Maria Jorgensen, B.A., Steven F. Kruger, B.A., and Bruce Furie, M.D., N.E. J. Med 305:242-248 (Jul. 30), 1981.

While specific embodiments of the present invention have been shown and described, many variations are possible. Various immunoassay techniques can be used. In all cases, one can determine the levels of human native prothrombin in plasma or serum in vitro to determine the condition and levels in the body of the individual from whom the plasma was taken and the same can be done in connection with human abnormal prothrombin levels.

Antisera can be made using conventional techniques known in the immunological areas. The host animal is preferably rabbit although other animals such as horse, goat, cow and the like can be used. Period of incubation or production of antibodies in the host animal can vary greatly as known in the art as can the level of antibodies produced in the sera taken from the animals. Monoclonal antibodies may also be used.

The specific volumes, buffers and the like used can vary as known in the art. Chromatography columns of diameters from 0.5 cm to 5 cm could be used. Flow rates through such columns could vary for 20 ml per hour to 200 ml per hour depending in part on column size. Alternatively, immunoabsorption could be carried out in a batchwise fashion. Buffer solutions containing Tris, borate, phosphate or other buffering agents with pH's in the range of pH 7-8.5 could be used depending upon application. Such buffer solutions could include in addition sodium chloride, nonionic detergents (e.g. Tween 20), proteolytic inhibitors (e.g. benzmidine), bacteriacidal agents (e.g. sodium azide), metal ions or chelating agents (e.g. EDTA) depending upon application. Immunoabsorption is preferably carried out at room temperature (20° C. to 25.6° C.).

The plasma tested in the radioimmunoassay of the present invention or other immunoassay is preferably prepared from freshly drawn blood treated with standard amounts of anticoagulant. Such anticoagulants include sodium citrate, heparin and others. Preferably under test conditions, standard amounts are added to the plasma in order to maintain test precision where quantitative determinations are made. Preferably plasma once prepared is stored frozen at ultra cold temperatures ranging from −30° C. to −70° C. if immunoassay is not to be performed immediately on the plasma or serum sample.

The recognition that levels of abnormal prothrombin in vitro are an indication of body disorders and means of body regulation is a feature of the invention as are the methods of producing the specific antibodies of this invention and the antibodies themselves.

Immunoassay kits can be prepared containing vials of the antibodies of this invention for use in assay techniques. For example, vials of labelled or unlabelled antibody specific to human native prothrombin and antibody specific to human abnormal prothrombin each in the presence of the other and in the presence of calcium ion, can be prepared and packaged along with other materials for use in RIA or other immunoassay kits. The volume of materials in such kits and the number of components of the kits can vary greatly. Such kits are often distributed along with instruction for carrying out immunoassay techniques to determine the presence of absence and quantitative amounts of the antigens which form antigen antibody complexes with the antibodies of the kits.

It has now been found that in a variety of disease states the levels of prothrombin and abnormal prothrombin are significantly altered from the noraml range. This has diagnostic value.

A facile process has been developed which allows rapid isolation of antibodies specific for prothrombin which do not bind to abnormal prothrombin. This is based upon the principle that prothrombin bound to agarose undergoes stabilization of a three-dimensional structure in the presence of metal ions. When metal ions are removed from prothrombin with EDTA, prothrombin undergoes a conformational transition. Conformation specific antibodies directed against the metal stabilized form of prothrombin are displaced during this conformational rearrangement. Thus anti-prothrombin antiserum is applied in Ca(II) to a column of prothrombin covalently coupled to agarose and purified by ligand elution affinity chromatography. Anti-prothrombin-Ca(II) (antibodies specific for native prothrombin) are eluted with EDTA. The bulk of the anti-prothrombin antibodies remain bound to the column matrix. These anti-prothrombin-Ca(II) antibodies bind prothrombin in the presence of Ca(II) but do not bind abnormal prothrombin.

A second antibody, specific for abnormal prothrombin, was isolated from anti-abnormal prothrombin antiserum by a process using sequential immunoabsorption employing affinity chromatography. A feature of this method includes the use of a semi-synthetic abnormal prothrombin analog, decarboxylated prothrombin, as an immunoabsorbent. Decarboxylated prothrombin was prepared by published methods via thermal decarboxylation. Anti-abnormal prothrombin antiserum was applied to aprothrombin-agarose column. Antibodies which failed to bind were applied to a decarboxylated prothrombin-agarose column. Antibodies which do bind to the column, anti-abnormal prothrombin antibodies, are eluted with guanidine hydrochloride. This antibody population binds only to abnormal prothrombin and not to prothrombin.

Using these immunochemicals as reagents specific radioimmunoassays for abnormal prothrombin and prothrombin in human plasma or serum have been developed. These radioimmunoassays involve a standard double antibody precipitation method and radioiodinated antigen. The assay for abnormal prothrombin is sensitive to 2 nanograms per milliliter. The limits of detection of abnormal prothrombin in the presence of 150 micrograms of prothrombin is 0.03 micrograms per milliliter. Normal plasma contains no abnormal prothrombin. Lower (0.2-8 micrograms per milliliter) of abnormal prothrombin are characteristic of various types of liver disease (hepatitis, cirrhosis, metastatic malignancy, primary hepatocellular carcinoma). Low to high levels of abnormal prothrombin (1-100 micrograms per milliliter) with correspondingly low levels of prothrombin correlated to the degree of vitamin K deficiency. Patients taking sodium warfarin have abnormal prothrombin levels in the range of 35 micrograms per milliliter and prothrombin levels of 10-30 micrograms per milliliter. This measurement of abnormal prothrombin and prothrombin can be used to identify (screen) and diagnose patients with disorders characterized by impaired vitamin K dependent carboxylation. These measurements can also be employed to monitor and control oral anticoagulant therapy. Lastly they can be used to distinguish between disorders of prothrombin synthesis and disorders of accelerated prothrombin catabolism/clearance.

While tests are normally carried out in serum or plasma they can also be carried out in whole blood with equivalent results obtained.

While warfarin monitoring has been described, similar results are obtained when other vitamin K antagonists and anticoagulants are monitored in accordance with the methods of this invention for monitoring oral use of warfarin.

As has been mentioned, in addition to conventional (polyclonal) antibodies purified from the serum of immunized host animals such as rabbits goats, monoclonal antibodies against native and abnormal prothrombin can be made and used in diagnostic methods. The production and use of such antibodies will now be described in greater detail.

Monoclonal Antibody Against Calcium Stabilized Native Prothrombin

Balb/c mice were immunized with an initial subcutaneous injection of 75 $\mu$g of human native prothrombin in complete Freund's adjuvant. Mice were the immunized biweekly with 50 $\mu$g of prothrombin in which 0.15M NaCl intravenously for the 3 consecutive days prior to fusion.

Spleen cells ($5 \times 10^7$) from immunized mice were fused with the Sp2/0 plasma cell line ($5 \times 10^6$) in 28% poly(ethylene glycol) 4000 (Sigma) by the method of Kohler and Milstein (1975) Nature 256, 495. The fused cells were suspended in hypoxanthineaminopterin-, and thymidine-containing (HAT) medium. The suspension was distributed into microtiter trays (Costar) at $3 \times 10^5$ cells/well. Supernatants were assayed for anti-prothrombin antibody after several weeks. Selected positive cultures were cloned by the limiting dilution method of McKearn (1980) *Monoclonal Antibodies* (Plenum Press, N.Y.). Cell lines producing anti-prothrombin antibodies were stored at $-70°$ C. in 95% bovine fetal calf serum and 5% dimethyl sulfoxide.

Of 496 wells plated with the cell-fusion suspension, growth was observed in 95% of the wells following selection with HAT medium. Anti-prothrombin antibody production was assayed with two separate assays described below.

Solid-Phase Radioimmunoassay of Anti-Prothrombin

Polystyrene tubes ($12 \times 75$ mm) were coated with purified goat anti-mouse immunoglobulin (20 $\mu$g/mL) in 0.05M borate buffer, pH 8.5, for 4 hours at 4° C. After being washed, the tubes were coated with 5% bovine serum albumin in 0.04M Tris-HCl, pH 7.2–0.14M NaCl. Hybridoma supernatants (100 $\mu$L) were added to the tubes and incubated at 37° C. for 18 hours. For comparison, Sp2 cell supernatant and mouse anti-prothrombin antiserum were used as negative and positive controls, respectively. After an extensive washing with 0.04M Tris-HCl, 0.14M NaCl, and 10 mM CaCl$_2$, pH 7.2, $^{125}$I-labeled prothrombin was added to each tube. After incubation at 37° C. for 24 hours, the tubes were washed with water and assayed for $^{125}$I in a Beckman 8000 scintillation spectrometer. Mouse anti-prothrombin antibodies that bound to immobilize goat anti-mouse immunoglobulin were detected by the binding of $^{125}$I-labeled prothrombin.

Solid-Phase Enzyme-Linked Immunoabsorbent Assay (ELISA) of Anti-Prothrombin

Microtiter plates (96 wells; Immunolon 2, Dynatech) were coated with human prothrombin at 20 $\mu$g/mL in 0.05M borate, pH 8.5, for 16 hours at 4° C. The plates were washed exhaustively with 0.05M Tris-HCl, pH 7.2 0.14M NaCl, 5 mM CaCl$_2$, 0.05% NaN$_3$, and 2% bovine serum albumin in the same buffer added to the wells for 30 minutes at 24° C. After an extensive washing with 0.05M Tris-HCl, pH 7.2, 0.14M NaCl, 5 mM CaCl$_2$ and 0.05% NaN$_3$, 50 $\mu$L of tissue culture supernatant or mouse polyclonal anti-prothrombin antiserum was added to the plate and incubated at 37° C. for one hour. The plates were extensively washed with 0.15M Tris-HCl, 7.2, 0.14M NaCl, 1.5 mM MgCl$_2$, 2 mM $\beta$-mercaptoethanol, 0.05% Tween20, and 0.05% NaN3. Fab fragments of sheep anti-mouse Ig (50 $\mu$L) conjugated to $\beta$-galactosidase in the above buffer were added. After the plates were incubated at 24° C. for 2 hours, they were washed with the same buffer 3 times. p-Nitrophenyl D-galactoside [50 $\mu$L in 0.05M sodium phosphate (pH 7.2), 1.5 mM MgCl$_2$ and 0.1M $\beta$-mercaptoethanol] was added to each well and the reaction developed over 30–60 minutes at 23° C. The absorbance at 405 nm was monitored on a Dynatech Mr 580 Micro-ELISA auto reader. Anti-prothrombin antibodies bound to immobilized prothrombin were detected.

Nine of the positive cultures were cloned by the method of limiting dilution, resulting in 42 anti-prothrombin-positive clones. Eight of these subclones were chosen for further investigation.

Antibody Purification

Hybrid clones producing anti-prothrombin antibodies of interest were injected intraperitoneally into Balb/c mice by standard methods. After 2–3 weeks, ascitic fluid was removed. Specific antibodies were purified from this fluid by affinity chromatography. Ascitic fluid (2 mL) was applied to a $6.5 \times 2$ cm column of prothrombin-agarose equilibrated in Tris-HCl, pH 8.1, 1M NaCl, and 7 mM CaCl$_2$. The eluate was monitored at 280 nm. The column was washed free of unbound protein; bound protein was eluted with either 0.05M Tris-SCl, pH 7.2, 0.5M NaCl, and 70 mM EDTA or 4M guanidine hydrochloride. Antibodies were dialyzed against 0.05M Tris-HCl, pH 7.2, 0.14M NaCl and stored at $-15°$ C.

Characterization of Monoclonal Antibodies

The immunoglobulin type and subclass of the antibodies were determined by Ouchterlony immunodiffusion with precipitating antisera. Ouchterlony immunodiffusion was performed by standard methods. Monoclonal antibody solutions (20 $\mu$L) and commercial typing sera (5 $\mu$L) were applied to appropriate wells prepared in 1% agarose, 0.05M Tris-HCl, pH 7.5, and 0.02% NaN$_3$.

The clones elaborated anti-prothrombin monoclonal antibodies of the IgG class. Seven of the antibodies had light chains and one was indeterminant. Most of the immunoglobulins were of the IgG$_1$ subclass. These results give further evidence for the clonal character of each of these cultures.

The antigenic specificity of the monoclonal antibodies from eight clones was evaluated by a competitive assay based on the solid-phase ELISA method. Antibodies from these clones bound immobilized human prothrombin; free prothrombin competed with bound prothrombin for antibody. By use of this competition assay the interaction of antibodies with prothrombin fragment 1, abnormal (des-$\gamma$-carboxy) prothrombin, thrombin, prethrombin 1, and bovine prothrombin were examined. All of the monoclonal antibodies bound fragment 1, the NH$_2$-terminal third of prothrombin, and none bound prethrombin 1, the COOH-terminal two-thirds of prothrombin. The antibodies did not bind to thrombin that had been treated with (p-amidinophenyl) methanesulfanyl fluoride. Antibodies derived from three of the clones cross-reacted significantly with abnormal prothrombin while the others did not. However, none of the antibodies cross-reacted equivalently with fragment 1 and prothrombin. Significantly higher concentrations (from 2-fold to 10-fold) of fragment 1 compared to prothrombin were required to inhibit 50% of antibody-immobilized prothrombin interaction. None of the monoclonal antibodies bound to bovine prothrombin.

Monoclonal antibodies derived from the culture supernatants of the eight clones were examined for prothrombin binding activity in the presence and absence of calcium. Three clones produced conformation-specific antibodies. Monoclonal antibodies from one of these clones (designated RL 1-3) bound prothrombin in the presence of 5 mN CaCl$_2$ but showed no significant binding in the presence of 7 mM EDTA. In contrast, antibodies from another clone bound prothrombin similarly in the presence of CaCl$_2$ or in the presence of EDTA. These experiments indicate that the monoclonal antibodies from clone RL1-3 are specific for the conformer of prothrombin stabilized by calcium ions.

Clone RL 1-3 has been deposited in the Agricultural Research Culture Collection (NRRL), Peoria, Ill. and given NRRL Accession Number HB8637.

Characteristics of Antibody-Prothrombin Interaction

The binding of purified RL 1-3 antibody with prothrombin was studied by using the solid-phase ELISA method of Frankel and Gerhard (1979) Mol. Immunol. 16, 101. The amount of anti-prothrombin bound to the plate was determined from a standard curve prepared on the basis of the binding of antibody of known concentration to wells coated with excess prothrombin. On the basis of these data, a Scatchard plot was prepared. The binding constant, $K_a$, was observed to be $2.3 \times 10^9 M^{-1}$. The binding curve was linear over the concentration range studied. This indicates a single population of antibody combining sites, anticipated for a monoclonal antibody preparation.

The relationship of the antigenic determinants against which monoclonal RL 1-3 antibody and polyclonal rabbit anti-prothrombin-Ca(II) antibody are directed was evaluated in a competition immunoassay. RL 1-3 antibody was displaced from prothrombin by anti-prothrombin CA(II), indicating that these antibodies compete for similar or overlapping sites in the fragment 1 domain.

Interaction of Conformation-Specific Antibodies with Prothrombin

The interaction of antibodies derived from the RL 1-3 clone and prothrombin was studied over a wide range of calcium concentrations. The ELISA method was employed. For elimination of contaminating calcium, plates containing immobilized prothrombin were washed with a buffer containing EDTA and then exhaustively washed with 0.05M Tris-HCl, pH 7.2–0.14M NaCl prepared with metal-free water. Antibody binding to prothrombin was calcium dependent. Maximal binding was observed at 0.9 CaCl$_2$ and half-maximal binding observed at 0.10 mM CaCl$_2$.

The effect of other cations on antibody-antigen interaction was evaluated by the same methods. In contrast to metal-free buffer, buffer containing Mg(II), Mn(II), Co(II), and Ca(II) support antibody-antigen interaction. Half-maximal antibody binding was similar for Ca(II), Mg(II), and Co(II). Lower concentrations of Mn(II) were effective in supporting antibody-prothrombin interaction. These data are in good accord with previous data obtained with polyclonal antibodies.

Monoclonal Antibody Against Abnormal Prothrombin

Balb/c mice were immunized with the subcutaneous injection of 25 μg of human abnormal prothrombin in complete Freund's adjuvant. Thirty and 37 days later, 10 μg of abnormal prothrombin were injected in saline. Spleen cell fusions with the Sp 2/0 plasma cell line were carried out by the method of Kohler and Milstein using 28% polyethylene glycol 2000, as previously described. Cells were cultured, selected, and their supernatants assayed using standard methods, as follows.

Cells secreting anti-abnormal prothrombin antibodies were identified with two solid phase ELISA systems using abnormal prothrombin and native prothrombin. Wells which showed significantly greater reactivity with abnormal native prothrombin than prothrombin were cloned by limiting dilution. One clone, designated J01-1, produced antibodies which bound to abnormal prothrombin but reacted minimally with native prothrombin. The monoclonal antibody was defined as an IgG$_1$ by Ouchterlony immunodiffusion using type specific antisera.

Clone J01-1 has been deposited in the ATCC and has been given ATCC Accession Number HB8638.

Purification of J01-1 Antibody

Because of the observations, described above, that the conformation-specific nature of antibodies to the prothrombin-Ca++ complex enables the affinity purification of these antibodies on prothrombin-Sepharose in the presence of Ca++, which subsequent elution with EDTA, purification of J01-1 antibody, which is specific for calcium-free abnormal prothrombin, was carried out using the reverse conditions. Prothrombin was coupled to cyanogen bromide-activated Sepharose 4B at a protein to resin ratio of 2 mg/ml. Two affinity columns were prepared in which the prothrombin was coupled either in the presence or absence of 6 mM EDTA.

J01-1 culture supernatant was concentrated 4-fold with an Amicon PM 30 membrane and dialyzed into TBS/EDTA (3 mM). This material (1.5 ml) was applied to each prothrombin-Sepharose column (1.0×2.3 cm) after equilibration with TBS/EDTA (3 mM). Antibody which bound was eluted with TBS/Ca++ (15 mM) after a 1 hour incubation in the same buffer.

The prothrombin binding activity was assayed by a direct binding ELISA. A standard curve was constructed from serial dilutions of the antibody preparation. Purified monoclonal antibody was concentrated in dialysis tubing using dry sucrose and evaluated for purity on 8.75% SDS polyacrylamide gels. The isolated J01-1 antibody migrated as a single band upon SDS and David gel electrophoresis.

Effect of Divalent Cations on Antibody-Prothrombin Interactions

Using the direct binding ELISA, the effect of Ca++, Mg++, and Mn++ on the dissociation of the antibody-antigen complex was examined. Immulon II plates containing prothrombin were washed twice with TBS, then 2% BSA/TBS/7 mM EDTA for 30 minutes at 23° C. EDTA and contaminating metals were removed from the wells by exhaustive washing with TBS made with water that had been rendered metal-free using a column containing Chelex 100 (BioRad). Purified additional antibody was eluted with 0.1M glycine, pH 2.5. Under the conditions established, all of the J01-1 antibody was removed from the tissue culture supernatant.

The results showed that increasing Ca++ concentrations were associated with decreasing antibody-antigen interaction. Half-maximal binding was observed at 0.9 mM $CaCl_2$. In contrast, half-maximal binding was observed at 3 mM $MnCl_2$. High concentrations of Mg++ had a limited effect on antibody-antigen displacement.

Effect of Calcium Ions on Antibody-Prothrombin Interaction

The interaction of J01-1 antibodies in tissue culture supernatant with prothrombin and abnormal prothrombin in the presence of absence of 5 mM $CaCl_2$ was evaluated using the solid phase sandwich ELISA. J01-1 antibodies bound to abnormal prothrombin in the presence of absence of calcium ions. Abnormal prothrombin, deficient in γ-carboxyglutamic acid, has impaired metal binding properties and does not undergo a metal-induced conformational transition. In contrast, J01-1 antibodies bound to prothrombin only in the presence of EDTA. No binding of antibody to prothrombin was detected in the presence of 5 mM $CaCl_2$. These results indicate that this monoclonal antibody, specific for abnormal prothrombin, is also conformation-specific for the calcium-free conformer of prothrombin.

Antigenic Determinants on Prothrombin

The ability of prothrombin and polypeptide fragments of prothrombin to inhibit the interaction of J01-1 antibody with abnormal prothrombin bound to a solid phase was evaluated using a competition ELISA. Abnormal prothrombin, fragment (1-39), fragment 1, and prothrombin in the presence of 7 mM EDTA bound effectively to the J01-1 antibody. Within experimental error, it would appear that J01-1 antibody bound equivalently to an antigenic determinant expressed on these polypeptides. In contrast, des-(1-44) prothrombin in the presence of 7 mM EDTA and prothrombin in the presence of 15 mM $CaCl_2$ did not bind to the antibody. These results indicate that the antigenic determinant against which J01-1 antibody is directed on prothrombin and abnormal prothrombin is contained within the $NH_2$-terminal 1 to 39 amino acid residues of prothrombin and is fully expressed on fragment (1-39).

Use of Antibodies Against Abnormal Prothrombin to Detect Primary Hepatocellular Carcinoma As discussed above, antibodies (polyclonal or monoclonal) reactive with human abnormal prothrombin and substantially unreactive with native human prothrombin can be used in immunoassays to detect the presence of abnormal prothrombin in a blood or other biological sample of a human patient; the detection of abnormal prothrombin enables a diagnosis of probable liver malfunction to be made. We have discovered that the quantification of abnormal prothrombin in a biological sample can further enable the diagnosis of probable primary hepatocellular carcinoma.

Primary hepatocellular carcinoma is a neoplasm known to be associated with synthesis of aberrant and ectopic proteins, including α-fetoprotein, abnormal vitamin $B_{12}$ binders, erythropoietin, and abnormal fibrinogens. Some of these proteins, in particular α-fetoprotein, have been used as diagnostic markers for the disease, for which early and accurate diagnosis is important in optimizing treatment and management. The presence of elevated abnormal prothrombin levels is in some respects a superior diagnostic marker for primary hepatocellular carcinoma than are some of the above proteins, as will now be discussed in greater detail.

Fifty Taiwanese patients and 26 American patients with biopsy-confirmed hepatocellular carcinoma were studied. Serum samples were obtained from these patients before therapy. Twenty-eight patients with biopsy-documented hepatitis B surface antigen-positive chronic active hepatitis and 17 patients with metastatic carcinoma involving the liver were also studied. The mean age of the patients with hepatocellular carcinoma was 54 years. Sixty-four percent of those patients were positive for hepatitis B surface antigen. When other serum markers of hepatitis B infection (hepatitis B surface antibody, hepatitis B core antibody, hepatitis B e antigen and hepatitis B e antibody) were measured in the Taiwanese patients, 41 of the 50 (82 percent) had evidence of hepatitis B infection.

Native prothrombin and abnormal prothrombin were measured in the serum of the patients using polyclonal antibodies, described above, in the above-described competitive radioimmunoassays. Interassay variability was less than ten percent. α-fetoprotein antigen and hepatitis B surface antigen were measured in serum by competition radioimmunoassays (-Feto-RIA Kit [Dainabot, Tokyo] and AUSRIA II Kit [Abbott Laboratories, Chicago]). Prothrombin times were determined in citrated plasma according to standard methods. The data were collected and analyzed by the CLINFO system (VAX 11/730 computer).

Because the values for abnormal prothrombin did not follow a normal distribution, statistical analyses included calculation of the geometric mean.

The distribution of abnormal-prothrombin antigen and native-prothrombin antigen among the 76 patients with hepatocellular carcinoma is shown in FIG. V (the abnormal prothrombin, which varies over five orders of magnitude, is shown on a logarithmic scale). In 91 percent (69 of 76) of these patients there was detectable abnormal prothrombin. The mean for all patients was 900 ng per milliliter (range, 0 to 67,000). There was no correlation between abnormal-prothrombin antigen and native-prothrombin antigen. The mean level of native-prothrombin antigen was 90,000±28,000 ng per milliliter which was not significantly different from the level of native prothrombin measured in normal subjects (108,000±19,000 ng per milliliter) P=0.34, Student's t-test).

The patients with hepatocellular carcinoma had normal levels of native-prothrombin antigen, unlike patients with vitamin K deficiency who, as discussed above, have depressed levels. The prothrombin-time index, also depressed in vitamin K deficiency was normal in 46 of 66 patients.

To exclude the possibility that the elevations of abnormal prothrombin in these patients reflected subclinical vitamin K deficiency, five patients were treated with parenteral doses of vitamin K (20 mg), given as a divided dose on two consecutive days, and their levels of abnormal-prothrombin antigen remeasured after seven days and compared with values in four patients with vitamin K deficiency (Table VII). The levels of serum abnormal-prothrombin antigen were not significantly changed in the patients with hepatoma, but were decreased in the patients with vitamin K deficiency, as expected.

TABLE VII

Effect of Vitamin K Therapy on Serum Abnormal-Prothrombin Antigen.

| PATIENT GROUP* | | ABNORMAL-PROTHROMBIN ANTIGEN (ng/ml) | |
|---|---|---|---|
| | | BEFORE THERAPY | AFTER THERAPY |
| Hepatoma | 1 | 260 | 452 |
| | 2 | 120 | 310 |
| | 3 | 3,900 | 2,500 |
| | 4 | 7,080 | 7,900 |
| | 5 | 322 | 420 |
| Vitamin K deficiency | 1 | 1,500 | 55 |
| | 2 | 660 | 50 |
| | 3 | 55 | 15 |
| | 4 | 30,000 | 910 |

*All patients were treated with parenteral vitamin K, and the level of abnormal-prothrombin antigen was determined seven days later. The patients with hepatoma received two injections of 10 mg each on consecutive days, and those with vitamin K deficiency received a single injection of 10 mg.

Levels of abnormal prothrombin and α-fetoprotein were measured in two patients who underwent surgical resection of their carcinoma. Before resection, one patient had a serum abnormal-prothrombin level of 11,000 ng per milliliter, which decreased to 15 ng per milliliter by one month after resection (FIG. VI). After 14 months the patient had no clinical or radiologic evidence of recurrence, and the abnormal-prothrombin antigen remained undetectable. At 17 months after resection, the concentration of abnormal-prothrombin antigen increased to 150 ng per milliliter and a CT scan documented recurrence of the hepatoma.

The level of a α-fetoprotein antigen correlated poorly with the clinical course. After resection, the α-fetoprotein level decreased from 230 to 108 ng per milliliter, with an unexplained increase to 1147 ng per milliliter at 14 months and a second decrease to 408 ng per milliliter at 17 months despite recurrence of cancer.

Another patient had a decrease in abnormal prothrombin from 6000 to 150 ng per milliliter one week after resection (FIG. VI). He was lost to follow-up, but returned 10 months later with clinical evidence of recurrence and a concentration of abnormal-prothrombin antigen of 4200 ng per milliliter. The α-fetoprotein-antigen levels in this patient reflected the clinical course.

Abnormal-prothrombin antigen was also measured in a 23-year-old woman with biopsy-confirmed α-fetoprotein-negative hepatocellular carcinoma who was treated with systemic chemotherapy (FIG. VI). This patient had a clinical response including a decrease in ascites, a decrease in liver size, improved appetite, and weight gain. The abnormal-prothrombin level decreased from a pretreatment value of 5500 ng per milliliter to 320 ng per milliliter.

Abnormal-prothrombin antigen was also measured in 28 patients with biopsy-proved hepatitis B surface antigen-positive chronic active hepatitis, a disorder associated with the development of primary hepatocellular carcinoma (FIG. VII). In these 28 patients the abnormal-prothrombin antigen levels (means, 10 ng per milliliter) were negligible. Abnormal-prothrombin antigen was also measured in 17 patients with metastatic carcinoma involving the liver—six patients with breast cancer, three with colon cancer, two with pancreatic cancer, three with lung cancer, two with lymphoma, and one with primary adenocarcinoma of unknown origin; serum levels of the antigen were increased, with a mean value of 42 ng per milliliter.

Sixty seven percent of the patients with primary hepatocellular carcinoma had abnormal-prothrombin levels above 300 ng per milliliter. This exceeds the levels of abnormal prothrombin measured in all patients with chronic active hepatitis, in all but one patient with metastatic carcinoma, and in 90 percent of the patients with acute hepatitis and cirrhosis previously studied. (Blanchard et al. (1981) N. Engl. J. Med. 305, 242).

The α-fetoprotein antigen was measured in the patients with hepatocellular carcinoma and plotted against abnormal-prothrombin antigen (FIG. VIII). There was a poor correlation between the two antigens ($r=0.3$). An α-fetoprotein-antigen level above 400 ng per milliliter has been reported to be highly suggestive of hepatocellular carcinoma, since it excludes elevations reported in most other malignant and non-malignant disorders. In 48 of the above 76 patients (63 percent), the -fetoprotein-antigen level was above 400 ng per milliliter; among the 28 with lower levels, 16 (57 percent) had abnormal-prothrombin levels above 300 ng per milliliter. When the results of both assays were combined, 64 patients (84 percent) had elevated levels of one or both serum antigens—values highly suggestive of primary hepatocellular carcinoma.

The α-fetoprotein and abnormal-prothrombin antigen levels were unrelated to the presence or absence of hepatitis surface antigen. The means value of serum abnormal prothrombin was 974 ng per milliliter (range, 0 to 67,000) in the patients who were surface antigen-negative.

The above results indicate that abnormal prothrombin is a serum tumor marker for primary hepatocellular carcinoma. This antigen is present in most patients with hepatoma and does not disappear with the administration of parenteral vitamin K. Therefore, these patients do not have vitamin K deficiency. Abnormal-prothrombin antigen, furthermore, is eliminated or reduced with tumor resection and with chemotherapy. This evidence supports the conclusion that abnormal prothrombin results from a hepatoma-induced defect in vitamin K-dependent carboxylation.

The above results indicate that large elevations of abnormal prothrombin can aid in discriminating between primary hepatocellular carcinoma and other liver disorders, including metastatic liver carcinoma. This comports with what is known of prothrombin synthesis; since only the hepatocyte synthesizes and carboxylates prothrombin, large elevations of abnormal-prothrombin antigen should occur only the malignant transformations of the hepatocyte. The low levels of abnormal prothrombin seen in nonmalignant hepatocellular disorders such as acute hepatitis, chronic active hepatitis, and cirrhosis may cause occasional difficulty in discriminating these diseases from hepatocellular carcinoma, so it is suggested that a threshold of about 300 ng per milliliter of serum (or the equivalent, if a dilution is used) as being highly suggestive of hepatoma. The very low levels of abnormal prothrombin that characterize chronic active hepatitis—a frequent precursor of hepatocellular carcinoma—may allow detection of malignant transformation in patients with chronic active hepatitis who are monitored for abnormal-prothrombin antigen levels.

The α-fetoprotein antigen and abnormal-prothrombin antigen can individually identify with high certainty approximately two-thirds of patients with primary hepatocellular carcinoma. These antigens measure alterations of different biochemical processes in the malignant hepatocyte. When used in combination, both tests offer information beyond that obtained with only a single tumor marker. If vitamin K deficiency can be excluded as a diagnostic consideration, these two tests can identify 84 percent of patients with primary hepatocellular carcinoma and are complementary tumor markers in this disease.

What is claimed is:

1. Isolated and purified antibodies which specifically bind to human abnormal prothrombin which form an antibody antigen complex with said human abnormal prothrombin in the presence or absence of calcium (II) and which are nonreactive with human native prothrombin.

2. A monoclonal antibody which specifically bind des-γ-carboxy human prothrombin and unreactive with native human prothrombin.

3. The monoclonal antibody of claim 2 wherein said antibody which specifically binds des-γ-carboxy human prothrombin in the presence of calcium ions.

* * * * *

UNITED STATES PATENT AND TRADEMARK OFFICE
CERTIFICATE OF CORRECTION

PATENT NO.   : 5,252,712

DATED        : October 12, 1993

INVENTOR(S)  : Bruce E. Furie, Barbara C. Furie, and
               Rita A. Blanchard It is certified that error appears in the above-identified patent and that said Letters Patent is hereby corrected as shown below:

On title page, item [56] "References Cited" PUBLICATIONS, column 2, line 4, replace "Disroders" with --Disorders--;

Under "OTHER PUBLICATIONS", page 2, column 2, line 2, replace "Rearch" with --Research--;

Column 2, line 42, replace "Cross immunoelectrophoresis" with --Crossed immunoelectrophoresis--;

Col. 2, line 55, replace "measured" with --measure--;

Col. 2, line 61, replace "protrombin" with --prothrombin--;

Col. 3, line 66, replace "of absence" with --or absence--;

Col. 4, line 62, replace "at level" with --at levels--;

Col. 4, line 66, replace "K antagonist" with --K antagonists--;

Col. 6, line 9, replace "while" with --with--;

Col. 6, line 11, replace "minimal" with --minimally--;

Col. 6, line 13, replace "On" with --One--;

Col. 6, line 48, replace "remove" with --removes--;

UNITED STATES PATENT AND TRADEMARK OFFICE
CERTIFICATE OF CORRECTION

PATENT NO. : 5,252,712

DATED : October 12, 1993

INVENTOR(S) : Bruce E. Furie, Barbara C. Furie, and
Rita A. Blanchard

It is certified that error appears in the above-identified patent and that said Letters Patent is hereby corrected as shown below:

Col. 7, line 4, replace "being" with --bind--;

Col. 7, line 53, replace "cell lins" with --cell lines--;

Col. 8, line 5, replace "0.1 g/ml" with --0.1 µg/ml--;

Col. 8, line 25, replace "Levels a vary" with --Levels vary--;

Col. 8, line 33, replace "complication" with --complications--;

Col. 8, line 44, replace "hemtologic" with --hematologic--;

Col. 8, line 54, replace "facitious" with --factitious--;

Col. 9, line 9, replace "citrate an" with --citrate and--;

Col. 9, line 54, replace "ovine" with --bovine--;

Col. 9, line 66, add before "growth", --human--;

UNITED STATES PATENT AND TRADEMARK OFFICE
CERTIFICATE OF CORRECTION

PATENT NO. : 5,252,712

DATED : October 12, 1993

INVENTOR(S) : Bruce E. Furie, Barbara C. Furie, and
Rita A. Blanchard

It is certified that error appears in the above-identified patent and that said Letters Patent is hereby corrected as shown below:

Col. 9, line 67, replace "(1961)" with --(1961))--;

Col. 10, line 25, replace "in placed of" with --in place of--;

Col. 10, line 45, replace "(1980)" with --(1980))--;

Col. 10, line 51, replace "the antibody was" with --The antibody was--;

Col. 10, line 60, replace "(1979)" with --(1979))--;

Col. 11, line 22, replace "(1978)" with --(1978))--;

Col. 11, lines 51-59, delete "As above...radioimmunoassay." These sentences have been duplicated.

Col. 12, line 55, replace "prepared" with --prepare--;

Col. 13, line 57, replace "plasma in patients" with --plasma from patients--;

Col. 13, line 32, replace "prothrom bin" with --prothrombin--;

Col. 14, line 4, replace "completion" with --competition--;

UNITED STATES PATENT AND TRADEMARK OFFICE
CERTIFICATE OF CORRECTION

PATENT NO.   : 5,252,712

DATED        : October 12, 1993

INVENTOR(S)  : Bruce E. Furie, Barbara C. Furie, and
               Rita A. Blanchard It is certified that error appears in the above-identified patent and that said Letters Patent is hereby corrected as shown below:

Col. 14, line 21, replace "coupled completely" with --could completely--;

Col. 14, line 43, replace "8.2 µg/." with --8.2 µg/ml.--;

Col. 14, line 64, replace "10% primary" to --10%. Primary--;

Col. 15, line 40, replace "varied these samples" with --varied in these samples--;

Col. 15, line 42, replace "protrombin" with --prothrombin--;

Col. 15, line 50, replace "protrombin" with --prothrombin--;

Col. 15, line 53, replace "protrombin" with --prothrombin--;

Col. 16, line 60, replace "immunoabsorbants" with --immunoabsorbents--;

Col. 17, line 6, replace "immunoabsorbant" with --immunoabsorbent--;

Col. 17, line 51, delete the single parenthesis after the word "carboxy";

UNITED STATES PATENT AND TRADEMARK OFFICE
CERTIFICATE OF CORRECTION

PATENT NO. : 5,252,712

DATED : October 12, 1993

INVENTOR(S) : Bruce E. Furie, Barbara E. Furie, and Rita A. Blanchard

It is certified that error appears in the above-identified patent and that said Letters Patent is hereby corrected as shown below:

Col. 19, TABLE III, under "PRIMARY DIAGNOSIS", line 2 No. 2, replace "Thrombophiebitis" with --Thrombophlebitis--;

Col. 20, TABLE III, No. 9, replace "290" with --29--;

Col. 20, TABLE III, No. 11, replace "theophylline-quarfenesin" with --theophylline-guanfenesin--;

Cols. 21-22, TABLE IV, No. 6, 4th col., replace "189" with --178--; and last entry in same line, after "0.62", insert --97--;

Cols. 21-22, TABLE IV, replace row Nos. 24-26 as follows:

| 24 | 58/F | Cirrhosis | 2.5 | 31 | 8 | 36 | 3.5 | 19.7 | 0.015 | 62 |
| 25 | 58/M | Cirrhosis | 5.1 | 56 | 33 | 83 | 2.6 | 14.6 | 0.00 | 82 |
| 26 | 55/F | Cirrhosis | 1.2 | 42 | 23 | 121 | 2.3 | 19.0 | 0.44 | 58 |

Col. 26, line 4, replace "noraml" with --normal--;

Col. 26, line 9, replace "The plasma" with --In the plasma--;

UNITED STATES PATENT AND TRADEMARK OFFICE
CERTIFICATE OF CORRECTION

PATENT NO. : 5,252,712

DATED : October 12, 1993

INVENTOR(S) : Bruce E. Furie, Barbara E. Furie, and
Rita A. Blanchard

It is certified that error appears in the above-identified patent and that said Letters Patent is hereby corrected as shown below:

Col. 27, line 43, replace "-30°C." with -- -40°C.--;

Col. 27, line 64, replace "of absence" with --or absence--;

Col. 28, line 1, replace "noraml" with --normal--;

Col. 28, line 32, replace "aprothrombin" with --a prothrombin--;

Col. 28, line 50, replace "Lower" with --Low levels--;

Col. 29, line 21, replace "the" with --then--;

Col. 29, lines 22-24, delete beginning with "in which...fusion" and replace with the following: "in complete Freund's adjuvant for 2-6 months. Following 2 months without immunization, mice were injected with 50 µg of prothrombin in 0.15 M NaCl intravenously for the 3 consecutive days prior to fusion"

Col. 29, line 40, replace "wells" with --walls--;

Col. 30, line 40, replace "Tris-SCl" with --Tris-HCl--;

Col. 31, line 67, replace "0.9 $CaCl_2$" with --0.9 mM $CaCl_2$--;

UNITED STATES PATENT AND TRADEMARK OFFICE
CERTIFICATE OF CORRECTION

PATENT NO. : 5,252,712

DATED : October 12, 1993

INVENTOR(S) : Bruce E. Furie, Barbara E. Furie, and Rita A. Blanchard

It is certified that error appears in the above-identified patent and that said Letters Patent is hereby corrected as shown below:

Col. 32, line 3, replace "buffer" with --buffers--;

Col. 32, line 63, replace "David" with --Davis--;

Col. 33, line 24, replace "of absence" with --or absence--;

Col. 33, line 27, replace "of absence" with --or absence--;

Col. 36, line 35, replace "means value" with --mean value--;

Col. 36, lines 36-37, replace "surface antigen-negative." with --surface-antigen-positive and 805 ng per milliliter (range, 0 to 23,000) in the patients who were surface antigen-negative.--

Col. 38, claim 2, line 8, replace "bind" with --binds--.

Signed and Sealed this

Twenty-fourth Day of May, 1994

BRUCE LEHMAN

Attest:

Attesting Officer

Commissioner of Patents and Trademarks